United States Patent
Solomons et al.

(10) Patent No.: US 11,622,991 B2
(45) Date of Patent: *Apr. 11, 2023

(54) PROTOCOL FOR TREATMENT OF LUPUS NEPHRITIS

(71) Applicant: Aurinia Pharmaceuticals Inc., Victoria (CA)

(72) Inventors: Neil Solomons, Victoria (CA); Robert B. Huizinga, North Saanich (CA)

(73) Assignee: Aurinia Pharmaceuticals Inc., Victoria (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/713,140

(22) Filed: Apr. 4, 2022

(65) Prior Publication Data
US 2022/0226428 A1 Jul. 21, 2022

Related U.S. Application Data

(63) Continuation of application No. 16/374,701, filed on Apr. 3, 2019, which is a continuation-in-part of application No. 15/835,219, filed on Dec. 7, 2017, now Pat. No. 10,286,036.

(60) Provisional application No. 62/541,612, filed on Aug. 4, 2017, provisional application No. 62/505,734, filed on May 12, 2017.

(51) Int. Cl.
| | | |
|---|---|---|
| *A61K 38/13* | (2006.01) | |
| *A61K 31/343* | (2006.01) | |
| *A61P 37/00* | (2006.01) | |
| *A61P 13/12* | (2006.01) | |
| *A61K 31/5377* | (2006.01) | |
| *A61K 31/573* | (2006.01) | |
| *A61B 5/20* | (2006.01) | |
| *A61B 5/00* | (2006.01) | |

(52) U.S. Cl.
CPC ............ *A61K 38/13* (2013.01); *A61K 31/343* (2013.01); *A61K 31/5377* (2013.01); *A61K 31/573* (2013.01); *A61P 13/12* (2018.01); *A61P 37/00* (2018.01); *A61B 5/201* (2013.01); *A61B 5/4848* (2013.01)

(58) Field of Classification Search
CPC .... A61K 31/365; A61K 31/573; A61K 38/13; A61K 31/5377; A61P 13/12
See application file for complete search history.

(56) References Cited

U.S. PATENT DOCUMENTS

| | | |
|---|---|---|
| 3,244,592 A | 4/1966 | Tadashi |
| 4,039,662 A | 8/1977 | Hecht |
| 4,117,118 A | 9/1978 | Harri |
| 4,120,949 A | 10/1978 | Bapatla |
| 4,409,205 A | 10/1983 | Shively |
| 4,649,047 A | 3/1987 | Kaswan |
| 4,744,980 A | 5/1988 | Holly |
| 4,795,643 A | 1/1989 | Seth |
| 4,804,539 A | 2/1989 | Guo |
| 4,839,342 A | 6/1989 | Kaswan |
| 4,865,846 A | 9/1989 | Kaufman |
| 4,883,658 A | 11/1989 | Holly |
| 5,051,402 A | 9/1991 | Kurihara |
| 5,075,104 A | 12/1991 | Gressel |
| 5,110,493 A | 5/1992 | Chyi |
| 5,188,826 A | 2/1993 | Chandrasekaran |
| 5,209,927 A | 5/1993 | Gressel |
| 5,227,372 A | 7/1993 | Folkman |
| 5,252,246 A | 10/1993 | Ding |
| 5,252,318 A | 10/1993 | Joshi |
| 5,326,761 A | 7/1994 | Rozier |
| 5,342,625 A | 8/1994 | Hauer |
| 5,360,611 A | 11/1994 | Robertson |
| 5,387,589 A | 2/1995 | Kulkarni |
| 5,401,510 A | 3/1995 | Robertson |
| 5,411,952 A | 5/1995 | Kaswan |
| 5,414,011 A | 5/1995 | Fu et al. |
| 5,441,732 A | 8/1995 | Hoeg |
| 5,474,979 A | 12/1995 | Ding |
| 5,496,861 A | 3/1996 | Rouse et al. |
| 5,540,931 A | 7/1996 | Hewitt |
| 5,558,876 A | 9/1996 | Desai |
| 5,576,025 A | 11/1996 | Akiyama et al. |
| 5,585,406 A | 12/1996 | Ding |
| 5,591,426 A | 1/1997 | Dabrowski |
| 5,599,534 A | 2/1997 | Himmelstein |
| 5,607,698 A | 3/1997 | Martin |
| 5,624,893 A | 4/1997 | Yanni |
| 5,643,870 A | 7/1997 | Boelsterli |

(Continued)

FOREIGN PATENT DOCUMENTS

| | | |
|---|---|---|
| EP | 0349061 B1 | 3/1995 |
| EP | 0868909 A2 | 10/1998 |

(Continued)

OTHER PUBLICATIONS

Mary Anne Dooley, Mycophenolate Mofetil Therapy in Lupus Nephritis: Clinical Observations, J Am Soc Nephrol 10: 833-839, 1999.*
Eurpean Medicine Agency, EMA, Assessment Report, voclosporin, accessed on Aug. 29, 2022, p. 8.*
Alamilla-Sanchez et al., (2021). "Mechanism of Action and Efficacy of Immunosupressors in Lupus Nephritis," International Journal of Nephrology and Renovascular Disease, 14:441-458.
Almaani et al., (2017). "Update on Lupus Nephritis," Clin J Am Soc Nephrol, 12:825-835.
Anders et al. Unmet medical needs in lupus nephritis: solutions through evidence-based, personalized medicine // Clin Kidney J. 2015. vol. 8(5). p. 492-502 [Found on Aug. 24, 2021], URL: https://www.ncbi.nlm.nih.gov/pmc/articles/PMC4581390/.

(Continued)

*Primary Examiner* — Julie Ha
*Assistant Examiner* — Erinne R Dabkowski
(74) *Attorney, Agent, or Firm* — Morrison & Foerster LLP

(57) ABSTRACT

By employing a pharmacodynamic dosing regimen, the effectiveness of a protocol for treatment of a proteinuric kidney disease with voclosporin can be maximized while minimizing undesirable side effects.

27 Claims, 2 Drawing Sheets

(56) References Cited

U.S. PATENT DOCUMENTS

| | | |
|---|---|---|
| 5,698,219 A | 12/1997 | Valdivia |
| 5,698,533 A | 12/1997 | Kang |
| 5,712,084 A | 1/1998 | Osgood |
| 5,741,512 A | 4/1998 | Hauer |
| 5,770,628 A | 6/1998 | Cantoro |
| 5,773,019 A | 6/1998 | Ashton |
| 5,798,333 A | 8/1998 | Sherman |
| 5,814,655 A | 9/1998 | Patel |
| 5,830,508 A | 11/1998 | MacKeen |
| 5,843,891 A | 12/1998 | Sherman |
| 5,866,159 A | 2/1999 | Hauer |
| 5,869,103 A | 2/1999 | Yeh |
| 5,886,030 A | 3/1999 | Maniar |
| 5,916,589 A | 6/1999 | Hauer |
| 5,962,014 A | 10/1999 | Hauer |
| 5,962,017 A | 10/1999 | Hauer |
| 5,998,365 A | 12/1999 | Sherman |
| 6,007,840 A | 12/1999 | Hauer |
| 6,024,978 A | 2/2000 | Hauer |
| 6,071,958 A | 6/2000 | Jimenez-Bayardo |
| 6,165,500 A | 12/2000 | Cevc |
| 6,193,985 B1 | 2/2001 | Sonne |
| 6,217,895 B1 | 4/2001 | Guo et al. |
| 6,241,969 B1 | 6/2001 | Saidi et al. |
| 6,254,860 B1 | 7/2001 | Garst |
| 6,254,893 B1 | 7/2001 | MacKeen |
| 6,284,235 B1 | 9/2001 | Foreman et al. |
| 6,309,569 B1 | 10/2001 | Farrar |
| 6,309,630 B1 | 10/2001 | Patel |
| 6,350,442 B2 | 2/2002 | Garst |
| 6,406,719 B1 | 6/2002 | Farrar |
| 6,565,777 B2 | 5/2003 | Farrar |
| 6,677,304 B2 | 1/2004 | Di Napoli |
| 6,713,081 B2 | 3/2004 | Robinson |
| 6,809,077 B2 | 10/2004 | Or |
| 6,814,966 B1 | 11/2004 | Wax |
| 6,828,356 B2 | 12/2004 | Su |
| 6,872,382 B1 | 3/2005 | Gamache |
| 6,923,988 B2 | 8/2005 | Patel |
| 6,953,776 B2 | 10/2005 | Di Napoli |
| 6,979,671 B2 | 12/2005 | Or |
| 6,982,282 B2 | 1/2006 | Lambert |
| 6,984,628 B2 | 1/2006 | Bakhit |
| 6,998,385 B2 | 2/2006 | Naicker et al. |
| 7,001,615 B1 | 2/2006 | Singh |
| 7,012,064 B2 | 3/2006 | Or |
| 7,012,065 B2 | 3/2006 | Or |
| 7,026,290 B1 | 4/2006 | Domb |
| 7,033,604 B2 | 4/2006 | Ueno |
| 7,048,946 B1 | 5/2006 | Wong et al. |
| 7,060,672 B2 | 6/2006 | Naicker et al. |
| 7,083,803 B2 | 8/2006 | Peyman |
| 7,087,237 B2 | 8/2006 | Peyman |
| 7,141,648 B2 | 11/2006 | Naicker et al. |
| 7,202,209 B2 | 4/2007 | Chang et al. |
| 7,214,664 B2 | 5/2007 | Mitra |
| 7,276,476 B2 | 10/2007 | Chang et al. |
| 7,288,520 B2 | 10/2007 | Chang et al. |
| 7,297,679 B2 | 11/2007 | Chang et al. |
| 7,332,472 B2 | 2/2008 | Naicker et al. |
| 7,351,741 B2 | 4/2008 | Weidner |
| 7,361,636 B2 | 4/2008 | Molino |
| 7,378,391 B2 | 5/2008 | Molino |
| 7,429,562 B2 | 9/2008 | Naicker et al. |
| 7,468,419 B2 | 12/2008 | Wu et al. |
| 7,482,327 B2 | 1/2009 | Hagerty et al. |
| 7,501,393 B2 | 3/2009 | Tien et al. |
| 7,511,013 B2 | 3/2009 | Molino et al. |
| 7,557,082 B2 | 7/2009 | Schiffman |
| 7,605,275 B2 | 10/2009 | Mudumba |
| 7,632,807 B2 | 12/2009 | Molino et al. |
| 7,655,625 B2 | 2/2010 | Brin |
| 7,745,400 B2 | 6/2010 | Feinerman et al. |
| 7,829,533 B2 | 11/2010 | Naicker et al. |
| 7,833,966 B2 | 11/2010 | Peyman |
| 7,846,468 B2 | 12/2010 | Wong |
| 7,846,478 B2 | 12/2010 | Ameye et al. |
| 7,846,479 B2 | 12/2010 | Fang |
| 7,893,040 B2 | 2/2011 | Loftsson |
| 8,003,124 B2 | 8/2011 | Varner |
| 8,043,628 B2 | 10/2011 | Wong |
| 8,067,433 B2 | 11/2011 | Chappell et al. |
| 8,071,120 B2 | 12/2011 | Wong |
| 8,207,129 B2 | 6/2012 | Schiffman |
| 8,211,855 B2 | 7/2012 | Chang |
| 8,435,544 B2 | 5/2013 | Mitra et al. |
| 8,535,694 B2 | 9/2013 | Mitra et al. |
| 9,017,725 B2 | 4/2015 | Mitra et al. |
| 9,492,499 B2 | 11/2016 | Jaynes et al. |
| 9,679,115 B2 | 6/2017 | Frey |
| 9,765,119 B2 | 9/2017 | Naicker et al. |
| 10,016,480 B2 | 7/2018 | Rudloff et al. |
| 10,149,886 B2 | 12/2018 | Jaynes et al. |
| 10,265,375 B2 | 4/2019 | Mitra et al. |
| 10,286,036 B2 | 5/2019 | Solomons et al. |
| 10,413,584 B1 | 9/2019 | Jaynes et al. |
| 10,472,394 B2 | 11/2019 | Naicker et al. |
| RE48,226 E | 9/2020 | Naicker et al. |
| 10,973,871 B2 | 4/2021 | Mitra et al. |
| 11,147,854 B2 | 10/2021 | Jaynes et al. |
| 2001/0041671 A1 | 11/2001 | Napoli |
| 2003/0018044 A1 | 1/2003 | Peyman |
| 2003/0044452 A1 | 3/2003 | Ueno |
| 2003/0143277 A1 | 7/2003 | Ameye et al. |
| 2003/0165545 A1 | 9/2003 | Huth |
| 2004/0048777 A1 | 3/2004 | Weidner |
| 2004/0106546 A1 | 6/2004 | Napoli |
| 2004/0110666 A1 | 6/2004 | Or |
| 2004/0156913 A1 | 8/2004 | Fang |
| 2004/0167197 A1 | 8/2004 | Rudolph et al. |
| 2004/0266669 A1 | 12/2004 | Wu |
| 2005/0014691 A1 | 1/2005 | Bakhit |
| 2005/0031697 A1 | 2/2005 | Vehige et al. |
| 2005/0048098 A1 | 3/2005 | Wong et al. |
| 2005/0059583 A1 | 3/2005 | Acheampong |
| 2005/0063996 A1 | 3/2005 | Peyman |
| 2005/0063997 A1 | 3/2005 | Peyman |
| 2005/0119160 A1 | 6/2005 | Keith |
| 2005/0152980 A1 | 7/2005 | Ausbom |
| 2005/0181018 A1 | 8/2005 | Peyman |
| 2005/0191334 A1 | 9/2005 | Wong et al. |
| 2005/0267423 A1 | 12/2005 | Johnson |
| 2005/0277584 A1 | 12/2005 | Tien |
| 2006/0034799 A1 | 2/2006 | Brines |
| 2006/0034892 A1 | 2/2006 | Ueno |
| 2006/0052340 A1 | 3/2006 | Tsuzuki |
| 2006/0067966 A1 | 3/2006 | Wong et al. |
| 2006/0069015 A1 | 3/2006 | Molino |
| 2006/0069016 A1 | 3/2006 | Molino |
| 2006/0074015 A1 | 4/2006 | Molino |
| 2006/0110428 A1 | 5/2006 | deJuan |
| 2006/0116428 A1 | 6/2006 | Jimenez-Bayardo |
| 2006/0148686 A1 | 7/2006 | Xia |
| 2006/0153885 A1 | 7/2006 | Korb et al. |
| 2006/0177430 A1 | 8/2006 | Bhushan |
| 2006/0183698 A1 | 8/2006 | Abelson |
| 2006/0198871 A1 | 9/2006 | Wong |
| 2006/0204543 A1 | 9/2006 | Wong et al. |
| 2006/0204548 A1 | 9/2006 | Nivaggioli et al. |
| 2006/0217309 A1 | 9/2006 | Naicker et al. |
| 2006/0228414 A1 | 10/2006 | Cook |
| 2006/0257450 A1 | 11/2006 | Mudumba |
| 2006/0257451 A1 | 11/2006 | Varner |
| 2006/0280774 A1 | 12/2006 | Wong et al. |
| 2007/0015691 A1 | 1/2007 | Chang |
| 2007/0015693 A1 | 1/2007 | Chang et al. |
| 2007/0020336 A1 | 1/2007 | Loftsson et al. |
| 2007/0043006 A1 | 2/2007 | Bingaman |
| 2007/0065479 A1 | 3/2007 | Zhang et al. |
| 2007/0077286 A1 | 4/2007 | Ishihara et al. |
| 2007/0078077 A1 | 4/2007 | Peyman |
| 2007/0087962 A1 | 4/2007 | Tien |
| 2007/0092539 A1 | 4/2007 | Jimenez-Bayardo |
| 2007/0105761 A1 | 5/2007 | Chappell et al. |

(56) References Cited

U.S. PATENT DOCUMENTS

| | | |
|---|---|---|
| 2007/0141115 A1 | 6/2007 | Kunzler |
| 2007/0149447 A1 | 6/2007 | Chang et al. |
| 2007/0167358 A1 | 7/2007 | Feinerman et al. |
| 2007/0191266 A1 | 8/2007 | Brin |
| 2007/0219127 A1 | 9/2007 | Walt |
| 2007/0299004 A1 | 12/2007 | Acheampong et al. |
| 2008/0009436 A1 | 1/2008 | Chang |
| 2008/0021101 A1 | 1/2008 | Jimenez-Bayardo |
| 2008/0039378 A1 | 2/2008 | Graham |
| 2008/0050420 A1 | 2/2008 | Wong |
| 2008/0050421 A1 | 2/2008 | Wong |
| 2008/0069859 A1 | 3/2008 | Wong |
| 2008/0070834 A1 | 3/2008 | Chang |
| 2008/0124377 A1 | 5/2008 | Wong et al. |
| 2008/0146497 A1 | 6/2008 | Graham et al. |
| 2008/0207494 A1 | 8/2008 | Chang et al. |
| 2008/0207495 A1 | 8/2008 | Graham |
| 2008/0249002 A1 | 10/2008 | Molino et al. |
| 2009/0062249 A1 | 3/2009 | Wong |
| 2009/0092665 A1 | 4/2009 | Mitra et al. |
| 2009/0131307 A1 | 5/2009 | Tien et al. |
| 2009/0148499 A1 | 6/2009 | Wong et al. |
| 2009/0196905 A1 | 8/2009 | Spada et al. |
| 2009/0264348 A1 | 10/2009 | Schiffman |
| 2010/0310642 A1 | 12/2010 | Mitra et al. |
| 2011/0300195 A1 | 12/2011 | Mitra et al. |
| 2013/0345185 A1 | 12/2013 | Mitra et al. |
| 2015/0157687 A1 | 6/2015 | Mitra et al. |
| 2015/0202150 A1 | 7/2015 | Mitra et al. |
| 2018/0325995 A1 | 11/2018 | Solomons et al. |
| 2019/0224275 A1 | 7/2019 | Solomons et al. |
| 2021/0077566 A1 | 3/2021 | Jaynes et al. |
| 2021/0338769 A1 | 11/2021 | Mitra et al. |

FOREIGN PATENT DOCUMENTS

| | | |
|---|---|---|
| EP | 0724452 B1 | 5/2000 |
| JP | 2005511538 A | 4/2005 |
| RU | 2317067 C2 | 2/2008 |
| WO | WO 1996014829 A1 | 5/1996 |
| WO | WO 2000040219 A1 | 7/2000 |
| WO | WO 2003032949 A1 | 4/2003 |
| WO | WO 2003033526 A2 | 4/2003 |
| WO | WO 2003033527 A2 | 4/2003 |
| WO | WO 2003051351 A1 | 6/2003 |
| WO | WO 2004089960 A2 | 10/2004 |
| WO | WO 2004096261 A1 | 11/2004 |
| WO | WO 2006001963 A1 | 1/2006 |
| WO | WO 2006028361 A1 | 3/2006 |
| WO | WO 2006036614 A2 | 4/2006 |
| WO | WO 2006066416 A1 | 6/2006 |
| WO | WO 2006086744 A1 | 8/2006 |
| WO | WO 2008002118 A1 | 1/2008 |
| WO | WO 2009048929 A1 | 4/2009 |
| WO | WO 2010126055 A1 | 11/2010 |
| WO | WO 2010144194 A1 | 12/2010 |
| WO | WO 2013054765 A1 | 4/2013 |
| WO | WO 2016061087 A1 | 4/2016 |
| WO | WO 2016061133 A1 | 4/2016 |
| WO | WO 2018207026 A2 | 11/2018 |
| WO | WO 2020046297 A2 | 3/2020 |
| WO | WO 2020082061 A1 | 4/2020 |
| WO | WO 2020210625 A1 | 10/2020 |
| WO | WO 2021224890 A1 | 11/2021 |

OTHER PUBLICATIONS

Appel et al., Mycophenolate Mofetil versus Cyclophosphamide for Induction Treatment of Lupus Nephritis, J Am Soc Nephrol 20: 1103-1112, 2009.

Astellas Pharma US, Inc., "PROGRAF® (tacrolimus) capsules, USP; PROGRAF® (tacrolimus) injection," Rx prescribing information (2015).

Aura, "Aurion Study Data Review," Presentation. Dated Sep. 27, 2016.

Aurinia Pharmaceuticals Inc, (2013). "Isotechnika Merger With Aurinia to Create Leading Nephrology Company," 2 pages.

Aurinia Pharmaceuticals, "Aurinia Announces Voclosporin Meets 48-Week Remission Endpoints, Achieving Highest Complete Remission Rate of Any Global Lupus Nephritis Study," Published Mar. 1, 2017. Retrieved from https://ir.auriniapharma.com/press-releases/detail/73/aurinia-announces-voclosporin-meets-48-week-remission. Retrieved on Dec. 12, 2018, 4 pages.

Aurinia Pharmaceuticals, "Aurinia highlights 48-week data from open-label AURION study," Published Mar. 27, 2017. Retrieved from https://ir.auriniaphanna.com/press-releases/detail/81. Retrieved on Dec. 12, 2018.

Aurinia Pharmaceuticals, "Aurinia Pharmaceuticals Announces Voclosporin Meets Primary Endpoint in Phase 11B AURA-LV Study in Lupus Nephritis," Published Aug. 15, 2016. Retrieved from https://ir.auriniapharma.com/press- releases/detail/49/aurinia-pharmaceuticals-announces-voclosporin-meets- primary. Retrieved on Dec. 12, 2018.

Aurinia Pharmaceuticals, "Aurinia releases additional 48-week data from the A URA-LV Study during late-breaking session," National Kidney Foundation. Dated Apr. 20, 2017. Retrieved from https://ir.auriniapharma.com/press- releases/detail/85/aurinia-releases-additional-48-week-data-from-the-aura-lv. Retrieved on Dec. 13, 2018.

Aurinia Pharmaceuticals, "Aurion DATA presentation," (2016) 6 pages.

Aurinia Pharmaceuticals, "Aurion study: 48-week data of multi-target therapy with Voclosporin, MMF and steroids for active lupus nephritis," Presentation. (2016).

Aurinia Pharmaceuticals, "Safety in recent global lupus nephritis trials, voclosporin and AURA," Presentation (2016) 16 pages.

Aurinia Pharmaceuticals, Clinical trials.gov, AURA-LV: Aurinia Urinary Protein Reduction Active—Lupus With Voclosporin (AURA-LV) (AURA-LV), NCT02141672, published online 2014.

Bao et al., "Successful treatment of class V+IV lupus nephritis with myltitarget therapy," J Am Soc Nephrol (2008) 19:2001-2010.

Boele-Schutte et al., (2017). "Measured GFR: not a gold, but a gold-plated standard," Nephro Dial Transplant, 32:ii80-ii84.

Busque et al., (2011). "The PROMISE Study: A Phase 2b Multi-center Study of Voclosporin (ISA247) Versus Tacrolimus in De Novo Kidney Transplantation," American Journal of Transplantation, 11:2675-2684.

Chang et al., (2021). "The ratio and difference of urine protein-to-creatinine ratio facilitate Yisk prediction of all-cause mortality," Scientific Reports, 11:7851, 13 pages.

Chen et al., "Short-term Outcomes of Induction Therapy With Tacrolimus Versus Cyclophosphamide for Active Lupus Nephritis: A Multicenter Randomized Clinical Trial," Am J Kidney Dis (2011) 57(2):235-244.

ClinicalTrials.gov, "History of Changes May 15, 2014 (v1) and Jun. 30, 2015 (v10) for Study: NCT02141672; AURA-LV: Aurinia Urinary Protein Reduction Active—Lupus with Voclosporin (AURA-LV)," submitted in Case IPR2022-00617, 18 pages.

ClinicalTrials.gov, (Jun. 30, 2015). "AURA-LV: Aurinia Urinary Protein Reduction Active—Lupus with Voclosporin (AURA-LV)," version 10, submitted in Case IPR2022-00617, 15 pages.

Corapi et al., "Comparison and evaluation of lupus nephritis response criteria in lupus activity indices and clinical trials," Arthritis Research & Therapy (2015) 17:110.

Cortes-Hernandez et al., "Long-term outcomes-mycophenolate mofetil treatment for Tupus nephritis with addition of tacrolimus for resistant cases," Nephrol Dial Transplant (2010) 25:3948-3956.

Curriculum Vitae of Dr. Edgar Jaimes submitted in Case IPR2022-00617 dated Jan. 18, 2022, 22 pages.

Dall'Era et al., "Identification of Biomarkers That Predict Response to Treatment of Lupus Nephritis with Mycophenolate Mofetil or Pulse Cyclophosphamide", Arthritis Care & Research (2011) 63(3):351-357.

Declaration of Dr. Edgar Jaimes submitted in Case IPR2022-00617 dated Feb. 18, 2022, 77 pages.

(56) References Cited

OTHER PUBLICATIONS

Declaration of Nathaniel E Frank-White submitted in Case IPR2022-00617 dated Feb. 18, 2022, 15 pages.

Dooley et al., "Speed of Remission with the use of Voclosporin, MMF and low dose steroids: results of a global lupus nephritis study," Abstract. Retrieved on https://acr.confex.com/acr/2016/late/papers/index.cgi?username=61565&password=329286. Retrieved on Oct. 3, 2016.

Dooley et al., "Speed of Remission with the Use of Voclosporin, MMF and Low Dose Steroids: Results of a Global Lupus Nephritis Study," Presentation. (2016) 30 pages.

Dooley et al., "Speed of Remission with the Use of Voclosporin, MMF and Low Dose Steroids: Results of a Global Lupus Nephritis Study." Nov. 15, 2016. available at http://c.eqcdn.com/_20c511591973b8d476d5c2e836374826/auriniapharma/db/246/850/pdf/2016-11-16+ACR+Speed+of+Remission+with+Voclosporin.pdf.

Excerpts from Comprehensive Clinical Nephrology Fifth Edition (2014) submitted in Case IPR2022-00617, 154 pages.

Excerpts from the Prosecution History of U.S. Pat. No. 10,286,036 submitted in Case IPR2022-00617 on Feb. 24, 2022, 275 pages.

Fu et al., "Clinical efficacy of cyclosporin a neoral in the treatment of pediatric lupus nephritis with heavy proteinuria," British Journal of Rheumatology (1998) 37:217-221.

Gentian, (2021). "A brief histroy of Glomerular Filtration Rate," retrieved online from <www.gentian.com/news/cystatin-c-glomerular-filtration-rate>, 7 pages.

Gheith et al., Next-generation calcineurin inhibitors in development for the prevention of organ rejection, Transplant Research and Risk Management 2014:6, pp. 24-30.

Ha et al., (2014). "Increased risk of everolimus-associated acute kidney injury in cancer patients with impaired kidney function," BMC Cancer, 14:906, 7 pages.

Hannah et al., "Tacrolimus use in lupus nephritis: A systematic review and meta-analysis," Autoimmunity Reviews (2016) 15:93-101.

Healthline, accessed on Jul. 1, 2019, Average Weight for Men: Age, Height, Body Composition & More.

HSS, Understanding Laboratory Tests and Results for Lupus (SLE), Rheumatology, pp. 1-7, published online 2015.

Huizinga et al., "AURION study: 24-week data of multi-target therapy with voclosporin, MMF and steroids for active lupus nephritis," Abstract. 10th European Lupus Meeting, Venice, Oct. 5-8, 2016.

Huizinga et al., "AURION Study: 48-week data of multi-target therapy with voclosporin, MMF and steroids for active lupus nephritis," Presented Mar. 26-29, 2017. Retrieved from http://c.eqcdn.com/_349da054eda96a4b6781a0902e2929ab/auriniaphanna/db/246/9I0/pdf/LUPUS+2017?+Presentation FINAL.pdf>. Retrieved on Dec. 12, 2018.

Huizinga et al., (2017). "Aurion study: 24-week data of multi-target therapy with Voclosporin, MMF and steroids for active lupus nephritis," LUPUS, 4(Suppl 1):A10-A11.

Ishii et al., "Influence of renal complications on the efficacy and adverse events of tacrolimus combination therapy in patients with systemic lupus erythematosus (SLE) during a maintenance phase: a single-centre, prospective study," Lupus Science & Medicine (2015) 2:e000091.

Jones, "Estimating Renal Function for Drug Dosing Decisions," Clin Biochem Rev (2011) 32:81-88.

Keane et al., (1999). "Proteinuria, Albuminuria, Risk, Assessment, Detection, Elimination (Parade): A Position Paper of the National Kidney Foundation," American Journal of Kidney Diseases, 33(5):1004-1010.

Kraaij et al., "TAC-TIC use of tacrolimus-based regimens in lupus nephritis," Lupus Science & Medicine (2016) 3:e000169.

Lee et al., "Relative efficacy and safety of tacrolimus, mycophenolate mofetil, and cyclophosphamide as induction therapy for lupus nephritis: a Bayesian network meta-analysis of randomized controlled trials," Lupus (2015) 24:1520-1528.

Levey et al., (1999). "A More Accurate Method To Estimate Glomerular Filtration Rate from Serum Creatinine: A new Prediction Equation," Annals of Internal Medicine, 120(6):461-470.

Li et al., (2012). "Mycophenolate mofetil or tacrolimus compared with intravenous cyclophosphamide in the induction treatment for active lupus nephritis," Nephro Dial Transplant, 27:1467-1472.

Ling et al., "Cytochrome P450 3A and P-glycoprotein drug-drug interactions with voclosporin," Br J Clin Pharmacol (2013) 77(6):1039-1050.

Ling et al., (2013). "Pharmacokinetics of Voclosporin in Renal Impairment and Hepatic Impairment," J Clin Pharmacology, 53(12):1303-1312.

Liu et al., "Multitarget Therapy for Induction Treatment of Lupus Nephritis A Randomized, Controlled Trial," Ann Intern Med (2015) 162(1):18-26.

Lorenz et al., "Treatment of active lupus nephritis with the novel immunosuppressant 15-deoxyspergualin: an open-label dose escalation study," Arthritis Research & Therapy 2011, 13:R36.

Lupus Foundation of America, (2021). "What is Lupus Nephritis?" retrieved online from <www.lupus.org/resources/what-is-lupus-nephritis>, 2 pages.

Mayo et al., "Voclosporin Food Effect and Single Oral Ascending Dose Pharmacokinetic and Pharmacodynamic Studies in Healthy Human Subject," The Journal of Clinical Pharmacology (2013) 53(8):819-826.

Miwa et al., "Steroid-Sparing Effect of Tacrolimus in the Maintenance Phase of Systemic Lupus Erythematosus: A Single-Center, Prospective Study," Clinical and Experimental Medical Sciences (2014) 2(3):75-86.

Miyasaka et al., "Efficacy and safety of tacrolimus for lupus nephritis: a placebo-controlled double-blind multicenter study," Mod Rheumatol (2009) 19:606-615.

Mok et al., "Effect of Renal Disease on the Standardized Mortality Ratio and Life Expectancy of Patients With Systemic Lupus Erythematosus," Arthritis & Rheumatism (2013) 65(8):2154-2160.

Mok et al., "Tacrolimus versus mycophenolate mofetil for induction therapy of lupus nephritis: a randomized controlled trial and long-term follow-up," Ann Rheum Dis (2016) 75:30-36.

Naesens M. et al. Calcineurin Inhibitor Nephrotoxicity // Clin J Am Soc Nephrol. 2009. vol. 4. p. 481-508 [Found on Aug. 24, 2021], URL: https://cjasn.asnjournals.org/content/4/2/481.

National Kidney Foundation, (2002). "Clinical Practice Guidelines for Chronic Kidney Dosease: Evaluation, Classification and Stratification," 356 pages.

Naughton C. A., Drug-Induced Nephrotoxicity. American Family Physician, Sep. 15, 2008, vol. 78, No. 6, pp. 743-750.

NICE: National Institute for Health and Care Excellence. Chronic kidney disease in adults: assessment and management, Jul. 23, 2014 (Jul. 23, 2014). [online], [retrieved on Jun. 12, 2019]. Retrieved from <http://nice.org.uk/guidance/cgl82>.

Novartis Pharmaceuticals Corporation , "Neoral® Soft Gelatin Capsules (cyclosporine capsules, USP) Modified; Neoral® Oral Solution (cyclosporine oral solution, USP) Modified," Rx prescribing information (2009).

Novartis, (2012). "Everolimus drug label," 36 pages.

Papp et al., (2008). "Efficacy of ISA247 in plaque psoriasis: a randomised, multicentre, double-blind, placebo-controlled phase III study," Lancet, 371:1337-42.

Parikh et al., (2016). "Current and Emerging Therapies for Lupus Nephritis," J Am Soc Nephrol, 27:2929-2939.

Pendergraft et al., "AURALV: Successful treatment of active lupus nephritis with voclosporin," Draft Preview of Abstract #6480. Retrieved on http://www.call4abstracts.com/asn16_system/c4a/preview.php Retrieved on Sep. 6, 2016.

Pendergraft et al., "AURALV: Successful treatment of active lupus nephritis with voclosporin," Presentation. Dated Nov. 19, 2016. 25 pages.

Petition for Inter Partes Review of Patent U.S. Pat. No. 10,286,036 submitted in Case IPR2022-00617, dated Feb. 24, 2022, 70 pages.

Powles, AV et al. Renal function after long-term low-dose cyclosporin for psoriasis. British Journal of Dermatology, 1990, vol. 122, pp. 665-669.

(56) References Cited

OTHER PUBLICATIONS

Rezaieyazdi et al., Efficacy of long-term maintenance therapy with mycophenolate mofetil in lupus nephritis, al. SpringerPlus 2014, 3:638, pp. 1-8.
Rovin et al., (2019). "A randomized, controlled double-blind study comparing the efficacy and safety of dose-ranging voclosporin with placebo in achieving remission in patients with active lupus nephritis," Kidney International, 95:219-231.
Rovin et al., Efficacy and Safety of Rituximab in Patients With Active Proliferative Lupus Nephritis, Arthritis & Rheumatism vol. 64, No. 4, Apr. 2012, pp. 1215-1226.
Solomons et al., "MP130 Aurion study: Multi-target therapy with Voclosporin, MMF and steroids for lupus nephritis," Nephrol Dial Transplant (2016) 31(suppl_1):i385.
Szeto et al., "Tacrolimus for the treatment of systemic lupus erythematosus with pure class V nephritis," Rheumatology (2008) 47:1678-1681.
Uchino et al., "Safety and potential efficacy of tacrolimus for treatment of lupus nephritis with persistent proteinuria," Clinical and Experimental Rheumatology (2010) 28:6-12.
us fda, (2007). "FDA Amendments Act of 2007," submitted in Case IPR2022-00617, 24 pages.
US FDA, (2022). "Orange Book: Approved Drug Products with Therapeutic Equivalence Evaluations," retrieved online from <hwww.accessdata.fda.gov/scripts/cder/ob/patent_info.cfm?Product_No=001&Appl_No=213716&Appl_type=N>, 2 pages.
USPTO Assignment History for Patent U.S. Pat. No. 10,286,036 submitted in Case IPR2022-00617 on Feb. 24, 2022, 2 pages.
Wilding, J et al. Prescribing anti diabetic drugs for patients with renal dysfunction. Prescriber, 2011, vol. 22, pp. 65-70.
Wofsy et al., Comparison of Alternative Primary Outcome Measures for Use in Lupus Nephritis Clinical Trials, Arthritis & Rheumatism vol. 65, No. 6, Jun. 2013, pp. 1586-1591.
Wolf et al. Development of Biomarker Models to Predict Outcomes in Lupus Nephritis // Arthritis Rheumatol. 2016. vol. 68(8). p. 1955-1963 [Found on Aug. 24, 2021], URL: https://www.ncbi.nlm.nih.gov/pmc/articles/PMC5201110/.
Yahya et al., "Aurion Study: 12 Week Data of Multi-Target Therapy with Voclosporin, MMF and steroids for lupus nephritis," Presentation. (2016) 19 pages.
Yahya et al., "Aurion study: 24-week data of multi-target therapy with voclosporin, MMF and steroids for active lupus nephritis," Aurion Lupus Final Abstract. Dated Oct. 31, 2016.
Yahya R. et al. Aurion study: preliminary results of voclosporin in lupus nephritis // Annals of the Rheumatic Diseases. 2016. vol. 75. p. 1049-1050 [Found on Aug. 25, 2021], URL: https://ard.bmj.com/content/75/Suppl_2/1049.3.
Yang et al., "Calcineurin inhibitors may be a reasonable alternative to cyclophosphamide in the induction treatment of active lupus nephritis: A systematic review and meta-analysis," Experimental and Therapeutic Medicine (2014) 7:1663-1670.
Zhang et al., "The effect of calcineurin inhibitors in the induction and maintenance treatment of lupus nephritis: a systematic review and meta-analysis," Int Ural Nephrol (2016) 48(5):731-743.
Adis R&D Profile "ISA247", Drugs RD, 8(2), 2007, pp. 103-112.
Anglade et al., "Next-Generation Calcineurin Inhibitors for Ophthalmic Indications," Expert Opin. Investig. Drugs, vol. 16, No. 10, pp. 1525-1540 (Oct. 2007).
Belousov et al., (2005). "Principles of LV dosing," Clinical Pharmacokinetics. Drug dosing: Special issue of the series "Rational pharmacotherapy", p. 274, 6 pages.
Benitez del Castillo et al., "Influence Of Topically Applied Cyclosporine A In Olive Oil On Corneal Epithelium Permeability," Cornea vol. 13(2): 136-40, Mar. 1994.
Blanco-Fuente et al., "Tanned Leather: A Good Model For Determining Hydrogels Bioadhesion," International Journal Of Pharmaceutics, vol. 138(1):103-112, Jul. 12, 1996.
Bonduelle et al., "Tissue Concentration Of Nanoencapsulated Radio-Labelled Cyclosporin Following Peroral Delivery In Mice Or Ophthalmic Application In Rabbits," European Journal of Pharmacology and Biopharmacology, vol. 42(5):313-319, Oct. 19, 1996.
Booth et al., "Sustained-Release Ophthalmic Drug Delivery Systems for Treatment of Macular Disorders," Drugs & Aging, vol. 24, No. 7, pp. 581-602 (Jul. 2007).
Borchard et al., "The Potential of Mucoadhesive Polymers in Enhancing Intestinal Peptide Drug Absorption. III: Effects of Chitosan-Glutamate and Carbomer on Epithelial Tight Junctions In Vitro," Journal of Controlled Release, 39(2-3), pp. 131-138 (May 1996).
Burgalassi et al., "Development and In Vitro/In Vivo Testing of Mucoadhesive Buccal Patches Releasing Benzydamine and Lidocaine," International Journal of Pharmaceuticals, 133(1-2), pp. 1-7 (May 14, 1996).
Chang et al., "The Effect Of Water-Soluble Vitamin E On Cyclosporine Pharmacokinetics In Healthy Volunteers," Clinical Pharmacology & Therapeutics, 59(3):297-303, Mar. 1996.
Cosar et al., "Topical Cyclosporine in Pediatric Keratoplasty," Eye & Contact Lens, vol. 29(2)103-107, Apr. 2003.
Dang et al., "Inhibition of Calcineurin or IMP Dehydrogenase Exerts Moderate to Potent Antiviral Activity against Norovirus Replication". Antimicrobial Agents and Chemotherapy, Nov. 2017 (Nov. 2017), vol. 61(11), pp. 1-17.
Decision—Institution of Inter Partes Review submitted before the USPTO Patent Trial and Appeal Board case IPR2022-00617, U.S. Pat. No. 10,286,036, filed Jul. 16, 2022, 32 pages.
Del Amo et al., "Current and Future Ophthalmic Drug Delivery Systems: A Shift to the Posterior Segment," Drug Discovery Today, vol. 13, Nos. 3/4, pp. 135-143 (Feb. 2008).
Dumont et al., "The Immunosuppressive And Toxic Effects Of FK-506 Are Mechanistically Related: Pharmacology Of A Novel Antagonist Of FK-506 And Rapamycin," Journal of Experimental Medicine, vol. 176(3):751-60, Sep. 1, 1992.
Extended European Search Report in EP Patent No. 10786539.6 dated Nov. 9, 2012, 5 pages.
Farouk et al., (2020). "The Many Faces of Calcineurin Inhibitor Toxicity—What the FK?," Adv. Chronic Kidney Dis., 27(1):56-66.
Feske et al., "Ca2+/Calcineurin Signalling In Cells Of The Immune System," Biochemical and Biophysical Research Communications vol. 311(4):1117-1132, Nov. 28, 2003.
Fukuhira et al., "Interfacial tension governs the formation of self-organized honeycomb-patterned polymer films", Soft Matter, 2009, 5, pp. 2037-2041. (Year: 2009).
Fuongfuchat et al., "Rheological Studies of the Interaction of Mucins with Alginate and Polyacrylate," Carbohydrate Research, 284(1), pp. 85-99 (Apr. 18, 1996).
Granelli-Piperno et al., "Lymphokine and Nonlymphokine mRNA Levels in Stimulated Human T Cells," J. Exp. Med., vol. 163, pp. 922-937 (Apr. 1986).
Gregory et al., "Compared with Cyclosporine, ISA247 Significantly Prolongs Renal-Allograft Survival in a Nonhuman Primate Model," Transplantation, vol. 78, No. 5, pp. 681-685, 2004.
Gummert et al., "Newer Immunosuppressive Drugs: A Review," Journal of the American Society of Nephrology, vol. 10(6):1366-80, Jun. 1999.
Hackett et al., "Assessing Ocular Irritation," Dermatoxicology, 5th Edition, edited by F.N. Marzulli and H.I. Maibach. Washington, D.C.: Taylor & Francis Publishers, Chapter 44, pp. 557-571 (1996).
Hackett et al., "Eye Irritation," Dermatoxicology, 4th Edition, edited by F.N. Marzulli and H.J. Maibach. Washington, D.C.: Hemisphere Publishing Corporation, Chapter 31, pp. 749-815 (1991).
Hackett et al., "Ophthalmic Toxicology and Assessing Ocular Irritation," Dermatoxicology, 5th Edition. Ed. F.N. Marzulli and H.I. Maibach. Washington, D.C.: Hemisphere Publishing Corporation, pp. 299-305 and 557-566. 1996.
Henriksen et al., "Bioadhesion Of Hydrated Chitosans: An In Vitro And In Vivo Study. International Journal of Pharmaceutics," vol. 145(1-2):231-240, Dec. 6, 1996.
Heo, (2021). "Voclosporin: First Approval," Drugs, 81(5):605-610, 6 pages.
Hu et al., "Biodegradable Amphiphilic Polymer-Drug Conjugate Micelles," Expert Opin. Drug Deliv., vol. 6, No. 10, pp. 1079-1090, Oct. 2009.

(56) References Cited

OTHER PUBLICATIONS

Hughes et al., "Topical and Systemic Drug Delivery to the Posterior Segments," Advanced Drug Delivery Reviews, vol. 57, pp. 2010-2032 (Nov. 10, 2005).
International Search Report based on PCT/US2008/79170 dated Dec. 31, 2008, 79 pages.
International Search Report based on PCT/US2010/33779 dated Jun. 29, 2010, 2 pages.
Issa et al., ((2013). "Calcineurin Inhibitor Nephrotoxicity: A Review and Perspective of the Evidence," Am J. Nephrol., 37:602-612.
Izci et al., "Histologic Characteristics And Local Cellular Immunity Of The Gland Of The Third Eyelid After Topical Ophthalmic Administration Of 2% Cyclosporine For Treatment Of Dogs With Keratoconjunctivitis Sicca," American Journal of Veterinary Research, vol. 63(5):688-694, May 2002.
Janoria et al., "Novel approaches to retinal drug delivery", Expert Opinion on Drug Delivery, Informa Healthcare, GB, vol. 4, pp. 371-388, Jul. 2007.
Kaswan et al., "Spontaneous Canine Keratoconjunctivitis Sicca. A Useful Model for Human Keratoconjunctivitis Sicca: Treatment With Cyclosporine Eye Drops," Archives of Ophthalmology, vol. 107(8):1210-1216, Aug. 1989.
Kaur et al., "Ocular Preparations: The Formulation Approach," Drug Development and Industrial Pharmacy, vol. 28, No. 5, pp. 473-493 (May 2002).
Kaur et al., "Penetration Enhancers and Ocular Bioadhesives: Two New Avenues for Ophthalmic Drug Delivery," Drug Development and Industrial Pharmacy, 28(4), 353-369 (2002).
Koevary, "Pharmacokinetics of Topical Ocular Drug Delivery: Potential Uses for the Treatment of Diseases of the Posterior Segment and Beyond," Current Drug Metabolism, vol. 4, No. 3, pp. 213-222 (Jun. 2003).
Komai et al., "The Three-Dimensional Organization of Collagen Fibrils in the Human Cornea and Sciera," Investigative Ophthalmology & Visual Science, vol. 32, No. 8, pp. 2244-2258 (Jul. 1991).
Lallemand et al., "Cyclosporine A Delivery to the Eye: A Pharmaceutical Challenge," European Journal of Pharmaceutics and Biopharmaceutics, vol. 56, pp. 307-318, 2003.
Langevin, D., "Micelles and Microemulsions," Annual Review of Physical Chemistry, 43, pp. 341-369, Oct. 1992.
Lee et al., "Pharmacokinetics and Organ Distribution of Cyclosporin A incorporated in Liposomes and Mixed Micelle," International Journal of Pharmaceutics, 191, pp. 87-93, 1999.
Liu et al., "Calcineurin is a Common Target of Cyclophilin-Cyclosporin A and FKBP-FK506 Complexes," Cell, vol. 66(4):807-815, Aug. 23, 1991.
Loftsson et al., "Topical Drug Delivery to the Posterior Segment of the Eye: Anatomical and Physiological Considerations," Pharmazie, vol. 63, No. 3, pp. 171-179 (Mar. 2008).
Lukyanov et al., "Micelles from lipid derivatives of water-soluble polymers as delivery systems for poorly soluble drugs," Advanced Drug Delivery Reviews 56, 1273-1289, 2004.
Lukyanov et al., "Polyethylene Glycol-Diacyllipid Micelles Demonstrate Increased Accumulation in Subcutaneous Tumors in Mice," Pharmaceutical Research. vol. 19(10):1424-1429, Oct. 2002.
Maeng et al., "Organozirconium Chemistry on Cyclosporin: A Novel Process for the Highly Stereoselective Synthesis of (E)-ISA24 7 (Voclosporin) and Close Analogues," Synthesis vol. 44, pp. 63-68, 2012 (Advanced Online Publication: Nov. 22, 2011).
Mainardes, "Colloidal Carriers for Ophthalmic Drug Delivery," Current Drug Targets, vol. 6, No. 3, pp. 363-371 (May 2005).
Mannermaa et al., "Drug Transport in Corneal Epithelium and Blood-Retina Barrier: Emerging Role of Transporters in Ocular Pharmacokinetics," Advanced Drug Delivery Reviews, vol. 58, Issue 11, pp. 1136-1163 (Sep. 16, 2006).
Marszall, "Measurement of effective HLB values using a non-ionic surfactant phenol titration method," Parfumerie, Kosmetik. vol. 60:444-448, Jan. 1979.

Maurice, "Drug Delivery to the Posterior Segment From Drops, Survey of Ophthalmology," vol. 47, Supp. 1, pp. S41-S52 (Aug. 2002).
Mitra, "Role of Transporters in Ocular Drug Delivery System", Pharmaceutical Research, vol. 26, No. 5, 17, pp. 1192-1196, Mar. 2009.
Mu et al., "Mixed Micelles Made Of Poly(Ethylene Glycol)-Phosphatidylethanolamine Conjugate And D-A-Tocopheryl Polyethylene Glycol 1000 Succinate As Pharmaceutical Nanocarriers For Camptothecin," International Journal of Pharmaceutics, vol. 306(1-2):142-149, Dec. 8, 2005.
Olivero et al., "Clinical Evaluation of 1 % Cyclosporine for Topical Treatment of Keratoconjunctivitis Sicca in Dogs," Journal of the American Veterinary Medical Association, vol. 199(8): 1039-1042, Oct. 15, 1991.
Rabinovich-Guilatt et al., "Cationic Vectors in Ocular Drug Delivery," Journal of Drug Targeting, vol. 12, No. 9-10, pp. 623-633 (Dec. 2004).
Rambali et al., "Influence of the Roll Compactor Parameter Settings and the Compression Pressure on the Buccal Bio-Adhesive Tablet Properties," International Journal of Pharmaceuticals, 220(1), pp. 129-140 (Jun. 4, 2001).
Robert et al., "Experimental-Method For Bioadhesive Testing Of Various Polymers," Acta Pharmaceutica Technologica-International Journal Of Drug Formulation And Biopharmaceutics, vol. 34(2):95-98, Jun. 1988.
Rommps. Chemistry Lexicon, 8th Edition. Franck'shce Verlagshandlung, Stuttgart, p. 1750, 1983.
Rusnak et al., "Calcineurin: Form and Function," Physiological Reviews, vol. 80(4):1483-1521, Oct. 2000.
Scheduling Order submitted before the USPTO Patent Trial and Appeal Board case IPR2022-00617, U.S. Pat. No. 10,286,036, filed Jul. 16, 2022, 12 pages.
Stepkowski, "Molecular Targets for Existing and Novel Immunosuppressive Drugs," Expert Reviews in Molecular Medicine, vol. 2, No. 4, pp. 1-23 (Jun. 21, 2000).
Su et al., "Effects of stability of PEGylated micelles on the accelerated blood clearance phenomenon", Drug Delivery and Translational Research, 2019, 6, pp. 66-75. (Year: 2019).
Sugita et al., "A New Calcineurin Inhibitor, Pimecrolimus, Inhibits The Growth Of *Malassezia* Spp.," Antimicrobial Agents and Chemotherapy, vol. 50(8):2897-2898, Aug. 2006.
Swei and Talbot, "Viscosity Correlation for Aqueous Polyvinylpyrrolidone (PVP) Solutions," Journal of Applied Polymer Science, 90(4), pp. 1153-1155, Aug. 26, 2003.
Tobyn et al., "Factors Affecting In-Vitro Gastric Mucoadhesion .1. Test Conditions And Instrumental Parameters," European Journal Of Pharmaceutics And Bio pharmaceutics. vol. 41(4):235-241, Aug. 1995.
Tobyn et al., "Factors Affecting In-Vitro Gastric Mucoadhesion .2. Physical Properties Of Polymers," European Journal Of Pharmaceutics And Biopharmaceutics. vol. 42(1):56-61, Jan. 1996.
Torchilin, "Micellar Nanocarriers: Pharmaceutical Perspectives," Pharmaceutical Research, vol. 24, No. I, pp. 1-16 (Jan. 2007).
Weiner et al., (2013). "Savvy Steroid Use," available online at <https://www.aao.org/eyenet/article/savvy-steroid-use>, 10 pages.
Weyenberg et al., "Characterization and In Vivo Evaluation of Ocular Minitablets Prepared with Different Bioadhesive Carbopol-Starch Components," European Journal of Pharmaceutics and Biopharmaceutics, 62(2), pp. 202-209 (Feb. 2006).
Winfield, "Opthalmic Products," Pharmaceutical Practice, Chapter 26, pp. 264-269, Churchill Livingstone, 2004.
Wu et al., "Characteristics Of D-Alpha-Tocopheryl PEG 1000 Succinate For Applications As An Absorption Enhancer In Drug Delivery Systems," Pharmaceutical Technology, vol. 23(10):52-60. Oct. 1999.
Yahya et al., (2016). "AURION Study: 12 week data of multi-target therapy with voclosporin, MMF and steroids for lupus nephritis," 10th European Lupus Meeting, Clinical and Experimental Rheumatology, vol. 34(4), Suppl. 99, 1 page.
U.S. Appl. No. 15/835,219, filed Dec. 7, 2017, by Solomons et al.
U.S. Appl. No. 16/374,701, filed Apr. 3, 2019, by Solomons et al.

(56) References Cited

OTHER PUBLICATIONS

Akhyani et al., "Efficacy and safety of mycophenolate mofetil vs. methotrexate for the treatment of chronic plaque psoriasis," J. of the European Academy of Dermatology & Venereology. (2010) 24: 1447-51.
American Academy of Ophthalmology, Uveitis treatment fails phase 3 trial (Jan. 2, 2013), https://www.aao.org/headline/uveitis-treatment-fails-phase-3-trial (Exhibit 2002).
American Kidney Fund, Serum creatinine test, https://www.kidneyfund.org/all-about-kidneys/tests/serum-creatinine-test?s.
Anglade et al., "A new agent for the treatment of noninfectious uveitis: rationale and design of three LUMINATE (Lux Uveitis Multicenter Investigation of a New Approach to Treatment) trials of steroid-sparing voclosporin," Clinical Ophthalmology. 2:693-702 (2008).
Aurinia Pharmaceuticals, Corporate Presentation, Sep. 27, 2016.
Aurinia Pharmaceuticals, National Kidney Foundation Spring Clinical Meeting, Presentation, Apr. 20, 2017.
Ayoub et al., "Calcineurin Inhibitors in the Treatment of Lupus Nephritis: A Hare Versus Turtle Story?", 28 J. Am. Soc Nephrol (2017) 3435-3437.
Beissert et al., "Treating pemphigus vulgaris with prednisone and mycophenolate mofetil: a multicenter, randomized, placebo-controlled trial," J Invest Dermatol. (2010) 130(8):2041-8.
Belimumab/Benlysta label (Jul. 2022) submitted in Case IPR2022-00617 on Feb. 24, 2022, 60 pages.
Bissonnette et al., "A randomized, multicenter, double-blind, placebo-controlled phase 2 trial of ISA247 in patients with chronic plaque psoriasis", J. Am. Academy of Dermatology. 54: 472-78 (2006).
Busque et al., Abstract# 149: ISA247: "Preliminary Results of a Phase IIb Multicentre, De Novo Renal Transplant Trial," American Journal of Transplantation. 7:185 (Supp. 2 2007).
Calizo et al., "Disruption of podocyte cytoskeletal biomechanics by dasatinib Teads to nephrotoxicity", Nature Communications. 10: 2061 (2019).
Calizo et al., "Disruption of podocyte cytoskeletal biomechanics by dasatinib Teads to nephrotoxicity": Supplementary Information (2019).
ClinicalTrials.gov identifier NCT00295425, "CYA Versus MMF for Treatment of Moderate-Severe Psoriasis," https://clinicaltrials.gov/ct2/show/NCT00295425, submitted in Case IPR2022-00617, 6 pages.
ClinicalTrials.gov identifier NCT00615173, History of Changes for Study: NCT00615173: Prospective, Randomized, Multicenter, Control Study to Assess the Efficacy and Safety of Tacrolimus in Induction and Maintenance Phase Treatment in Lupus Nephritis, https://clinicaltrials.gov/ct2/history/NCT00615173, submitted in Case IPR2022-00617, 4 pages.
ClinicalTrials.gov identifier NCT01224041, "Study to Evaluate the Efficacy of Tacrolimus in Rheumatoid Arthritis Patients Shown Unsuccessful Response to Methotrexate," https://clinicaltrials.gov/ct2/show/NCT01224041, submitted in Case IPR2022-00617, 6 pages.
ClinicalTrials.gov identifier NCT01316133, History of Changes for Study: NCT01316133: A Study to Evaluate the Efficacy and Safety of Tacrolimus With Steroid in Korean Lupus Nephritis Patients (APPLE), https://clinicaltrials.gov/ct2/history/NCT01316133, submitted in Case IPR2022-00617, 4 pages.
ClinicalTrials.gov identifier NCT01328834, History of Changes for Study: NCT01328834: "Efficacy and Safety of Tacrolimus Sustained-release Capsules in Induction Treatment in Refractory Lupus Nephritis," https://clinicaltrials.gov/ct2/history/NCT01328834, submitted in Case IPR2022-00617, 4 pages.
ClinicalTrials.gov identifier NCT01342016, A Study to Compare the Efficacy and Safety of Tacrolimus Capsules With Leflunomide Tablets in Lupus Nephritis Patients, https://clinicaltrials.gov/ct2/show/NCT01342016, submitted in Case IPR2022-00617, 7 pages.
ClinicalTrials.gov identifier NCT01499355, BIIB023 Proof-of-Concept Study in Participants With Lupus Nephritis (ATLAS), https://clinicaltrials.gov/ct2/show/NCT01499355, submitted in Case IPR2022-00617, 8 pages.

ClinicalTrials.gov identifier NCT01511003, History of Changes for Study: NCT01511003: A Study is to Assess Efficacy and Safety of Tacrolimus in Active Rheumatoid Arthritis Patients Who Showed Unsuccessful Response to Existing Disease Modifying Antirheumatic Drugs (DMARDs) (Treasure), https://clinicaltrials.gov/ct2/history/NCT01511003, submitted in Case IPR2022-00617, 5 pages.
ClinicalTrials.gov identifier NCT02176486, History of Changes for Study: NCT02176486: Safety, Tolerability and Pharmacokinetics of Multiple Rising Doses of Ixazomib in Lupus Nephritis (LN), https://clinicaltrials.gov/ct2/history/NCT02176486, submitted in Case IPR2022-00617, 18 pages.
ClinicalTrials.gov identifier NCT02260934, History of Changes for Study: NCT02260934: Rituximab and Belimumab for Lupus Nephritis (Calibrate), https://clinicaltrials.gov/ct2/history/NCT02260934, submitted in Case IPR2022-00617, 37 pages.
ClinicalTrials.gov identifier NCT02547922, History of Changes for Study: NCT02547922: Safety and Efficacy of Two Doses of Anifrolumab Compared to Placebo in Adult Subjects With Active Proliferative Lupus Nephritis (TULIP-LN1), https://clinicaltrials.gov/ct2/history/NCT02547922, submitted in Case IPR2022-00617, 25 pages.
ClinicalTrials.gov identifier NCT02550652, "History of Changes for Study: NCT02550652: A Study to Evaluate the Safety and Efficacy of Obinutuzumab Compared With Placebo in Participants With Lupus Nephritis (LN)," https://clinicaltrials.gov/ct2/history/NCT02550652, submitted in Case IPR2022-00617, 38 pages.
ClinicalTrials.gov identifier NCT02630628, History of Changes for Study: NCT02630628: "Efficacy and Safety of Tacrolimus Versus Mycophenolate in Lupus Nephritis," https://clinicaltrials.gov/ct2/history/NCT02630628; submitted in Case IPR2022-00617, 4 pages.
ClinicalTrials.gov identifier NCT05221411, Tacrolimus Versus Mycophenolate for Autoimmune Hepatitis Patients With Incomplete Response on First Line Therapy (Tailor), https://clinicaltrials.gov/ct2/show/NCT05221411, submitted in Case IPR2022-00617, 9 pages.
Decision Denying Patent Owner's Request for Rehearing of Decision Granting Institution of Inter Partes Review, dated Oct. 20, 2022, 12 pages.
Declaration of Abdul Halim Abdul Gafor, MBBS, in Case IPR2022-00617 dated Oct. 27, 2022, 5 pages.
Declaration of Dr. Casey M. Kraning in Support of Patent Owner's Motion for Pro Hac Vice Admission, dated Aug. 25, 2022, 8 pages.
Declaration of Laura Veasey, submitted in Case IPR2022-00617 dated Oct. 26, 2022, 5 pages.
Declaration of Neil Solomons, M.D. submitted in Case IPR2022-00617 dated Oct. 26, 2022, 9 pages.
Declaration of Raymond O. Cruitt, submitted in Case IPR2022-00617 dated Nov. 4, 2022, 17 pages.
Declaration of Robert Huizinga, Ph.D., R.N., Cneph(C), submitted in Case IPR2022-00617 dated Oct. 26, 2022, 9 pages.
Declaration of Rosnawati Yahya, MBChB, in Case IPR2022-00617 dated Oct. 27, 2022, 5 pages.
Declaration of Sushrut S. Waikar, M.D., M.P.H., dated Nov. 4, 2022, 107 pages.
Dekkers et al., "Effects of the sodium-glucose co-transporter 2 inhibitor dapagliflozin in patients with type 2 diabetes and Stages 3b-4 chronic kidney disease", Nephrol Dial Transplant. (2018) 33: 2005-2011.
Dobronravov et al., "Remission of Active Lupus Nephritis with Voclosporin: Results of the AURA-LV Study," EULAR 2017, Abstract.
Dobronravov et al., "Remission of Active Lupus Nephritis with Voclosporin: Results of the AURA-LV Study," EULAR 2017, Oral Presentation.
Dooley et al., "Speed of Remission with the Use of Voclosporin, MMF and Low Dose Steroids: Results of a Global Lupus Nephritis Study," ACR/ARHP Annual Meeing (2016) Abstract 5L.
Dumont, "ISAtx-247 Isotechnika/Roche," Current Opinion in Investigational Drugs 5:542-50 (2004).
Dykes, Lana, "FDA Approves First Oral Therapy Voclosporin for Lupus Nephritis," Rheumatology Network (Jan. 25, 2021), https://www.rheumatologynetwork.com/view/fda-approves-first-oral-therapy-voclosporin-for-lupus-nephritis.

(56) References Cited

OTHER PUBLICATIONS

European Medicines Agency, EMA, Lupkynis, International non-proprietary name: voclosporin, pp. 1-192, published online Jul. 2022.
FDA approves Lupkynis, first-ever oral therapy for lupus nephritis, Healio Rheumatology (Jan. 22, 2021), https://www.healio.com/news/rheumatology/20210123/fda-approves-lupkynis-firstever-oral-therapy-for-lupus-nephritis.
FDA Approves Lupkynis: FDA Approves Lupkynis (voclosporin) for Adult Patients with Active Lupus Nephritis, Drugs.com (Jan. 22, 2021), https://www.drugs.com/newdrugs/fda-approves-lupkynis-voclosporin-adult-patients-active-lupus-nephritis-5429.html.
Furie et al., "Efficacy and Safety of Abatacept in Lupus Nephritis: A Twelve-Month, Randomized, Double-Blind Study," 66 Arthritis & Rheumatology 379-89 (2014).
Furie et al., "Lessons Learned From the Clinical Trials of Novel Biologies and Small Molecules in Lupus Nephritis," Seminars in Nephrology. (2015) 35: 509-20.
Gaston et al., ISA247: A Novel Calcineurin Inhibitor (CNI) A Promising Safety Profile with Enhanced Efficacy, PROMISE Study Isotechnika Inc. (2006).
Gupta et al., Pharmacokinetics and Pharmacodynamics of ISA247 in a Phase III, Randomized, Multicentre, Double-Blind, Placebo-Controlled Study, SPIRIT Study Isotechnika Inc., submitted in Case IPR2022-00617, 9 pages.
Herrington et al., UK Kidney Association Clinical Practice Guideline: Sodium-Glucose Co-transporter-2 (SGLT-2) Inhibition in Adults with Kidney Disease, UK Kidney Association 1-125 (2021).
Holtkamp et al., "An acute fall in estimated glomerular filtration rate during treatment with losartan predicts a slower decrease in long-term renal function," 80 Kidney Int'l 282-87 (2011).
Houssiau, Biologic Therapy in Lupus Nephritis, Nephron Clinical Prac. (2014) 128: 255-260.
Huizinga et al., "AURION study: 12-week data of multi-target therapy with voclosporin, MMF and steroids for active lupus nephritis," Presentation, Europen Lupus Meeting 2016.
Huizinga et al., "Early Renal Response Biomarkers in Lupus Nephritis: Data from the AURION and AURA Trials," ASN Oct. 2017, Abstract.
Huizinga et al., "Early Renal Response Biomarkers in Lupus Nephritis: Data from the AURION and AURA-LV Trials," ASN Oct. 2017, Poster.
Kirsten et al., "Inclusion and exclusion criteria in phase III trials with systemic agents in psoriasis: the external validity of drug development," British J. of Dermatology. 175: 636-38 (2016).
Memorial Sloan Kettering Cancer Center biography of Edgar A. Jaimes, MD, https://www.mskcc.org/cancer-care/doctors/edgar-jaimes.
Mittal et al., "Pilot Study to Evaluate the Efficacy and Safety of Oral Tacrolimus in Adult Patients With Refractory Severe Plaque Psoriasis," 20 J. of Cutaneous Med. & Surgery 228-32 (2016).
Mysler et al., Efficacy and Safety of Ocrelizumab in Active Proliferative Lupus Nephritis: Results From a Randomized, Double-Blind, Phase III Study, Arthritis & Rheumatology (2013) 65:2368-79.
National Kidney Foundation, Tests to Measure Kidney Function, Damage and Detect Abnormalities (Last Reviewed Sep. 20, 2022), https://www.kidney.org/atoz/content/kidneytests.
Nieto et al., "Con: The use of calcineurin inhibitors in the treatment of lupus nephritis," 31 Nephrol Dial Transplant 1567-1571 (2016).
Notice of Stipulation to Extend Due Dates 1-3, dated Sep. 13, 2022, 3 pages.
Notification of Receipt of Precedential Opinion Panel (POP) Request, filed Aug. 10, 2022, 2 pages.
Order denying Precedential Opinion Panel (POP) Request, in Case IPR2022-00617, issued on Oct. 5, 2022, 2 pages.
Papp et al., "P33: A Phase III, randomized, multicenter, double-blind, placebo-controlled study of ISA247 in plaque psoriasis patients", J. Am. Academy of Dermatology. 54: AB9 (Supp. 2006).
Parikh et al., "Treatment of Active Lupus Nephritis with Voclosporin: Rapid Remission over 48 Weeks. Data from the AURA-LV Study," NKF Apr. 5, 2017, Poster.
Patent Owner's Amended Notice of Deposition of Dr. Edgar A. Jaimes, dated Sep. 14, 2022, 3 pages.
Patent Owner's Response, dated Nov. 4, 2022, 76 pages.
Patent Owner's Second Amended Notice of Deposition of Dr. Edgar A. Jaimes, dated Oct. 13, 2022, 3 pages.
Patent Owner's Updated Exhibit List, dated Nov. 4, 2022, 9 pages.
Patent Owner's Exhibit List, in Case IPR2022-00617, submitted on Jun. 16, 2022, 3 pages.
Patent Owner's Objections to Petitioner's Evidence, dated Aug. 9, 2022, 14 pages.
Patent Owner's Preliminary Response, in Case IPR2022-00617, submitted on Jun. 16, 2022, 64 pages.
Patent Owner's Request for Rehearing of the Institution Decision, dated Aug. 9, 2022, 20 pages.
Physicians' Desk Reference®, Abatacept/ORENCIA label (Dec. 2013) 702-10 (69th ed. 2005).
Precedential Opinion Panel Request, dated Aug. 9, 2022, 1 page.
Press Release, Drugs.com, "FDA Approves Rituxan—The First Targeted B-Cell Therapy for Treatment of Moderate-to-Severe Rheumatoid Arthritis" (Feb. 28, 2006), https://www.drugs.com/newdrugs/fda-approves-rituxan-first-targeted-b-cell-therapy-moderate-severe-rheumatoid-arthritis-394.html.
Press Release, FDA, "FDA approves new drug to treat multiple sclerosis" (Mar. 29, 2017), https://www.fda.gov/news-events/press-announcements/fda-approves-new-drug-treat-multiple-sclerosis#:~:text=On.
Qin et al., "Evaluating tacrolimus treatment in idiopathic membranous nephropathy in a cohort of 408 patients," BMC Nephrology. 18:2 (2017).
Rahman et al., "Classical to Current Approach for Treatment of Psoriasis: A Review," Endocrine, Metabolic & Immune Disorders—Drug Targets. (2012) 12:287-302.
Rovin et al., Efficacy and safety of voclosporin versus placebo for lupus nephritis (AURORA 1): a double-blind, randomised, multicentre, placebo-controlled, phase 3 trial, Lancet. 397: 2070-80 (2021).
Rovin et al., "Efficacy and safety of voclosporin versus placebo for lupus nephritis (AURORA 1): a double-blind, randomised, multicentre, placebo-controlled, phase 3 trial," Lancet. 397:2070-80 (Supp. App. 2021).
Ryan & Menter, "Recent and future developments in targeted therapy," in Psoriasis: Diagnosis and Management 249-67 (Wolfram Sterry et al. eds., 2015).
Sanders et al., "An international, phase III, randomized trial of mycophenolate mofetil in myasthenia gravis," Neurology. (2008) 71(6):400-6.
Solomons et al., "AURA-LV Post-Study Long-Term Outcomes," ERA Jun. 7, 2019, poster.
Stalder et al., "In Vivo Evaluation of the Novel Calcineurin Inhibitor ISATX247 in Non-Human Primates," J. of Heart & Lung Transplantation. (2003) 22:1343-52.
The European FK 506 Multicentre Psoriasis Study Group, "Systemic Tacrolimus (FK 506) Is Effective for the Treatment of Psoriasis in a Double-blind, Placebo-Controlled Study," 132 Archives of Dermatology 419-23 (1996).
Transcript from Deposition of Dr. Edgar Jaimes (dated Oct. 18, 2022), submitted in Case IPR2022-00617 on Feb. 4, 2022, 301 pages.
Tumlin et al., Voclosporin therapy in active lupus nephritis: reduced hypertension and electrolyte complications with CNI treatment [abstract]. 2017th ed. vol. 32, European renal association—European dialysis and transplant association Madrid Spain: Nephrology Dialysis Transplantation; 2017.
Tumlin et al., "Steroid Sparing Efficacy of Voclosporin in Active Lupus Nephritis: Stable Kidney Function and Blood Pressure without Electrolyte Complications at 48 Weeks." ERA-EDTA 2017, Presentation. Jun. 4, 2017.
Voclosporin approved by FDA to treat lupus nephritis, European Pharmaceutical Review (Jan. 25, 2021), https://www.europeanpharmaceuticalreview.com/news/140764/voclosporin-approved-by-fda-to-treat-lupus-nephritis/.

(56) References Cited

OTHER PUBLICATIONS

Voclosporin/Lupkynis label (Jan. 2021) submitted in Case IPR2022-00617 on Feb. 24, 2022, 24 pages.
Waikar et al., "Creatinine Kinetics and the Definition of Acute Kidney Injury," J. Am. Soc Nephrol. 20:672-79 (2009).
Yatscoff et al., Abstract# 1215: Phase2, Randomized, Multicenter, Open-Label Study of ISA247 and Neoral® In Post-Renal Transplant Patients, Am. J. of Transplantation 3:463 (2003).
Patent Owner and Petitioner's Joint Motion to Terminate Proceeding in Case IPR2022-00617, dated Jan. 3, 2023, 6 pages.
Patent Owner and Petitioner's Joint Request to File Settlement Agreement as Business Confidential Information under 35 U.S.C. § 317(b) and 37 C.F.R. § 42.74(c) in Case IPR2022-00617, dated Jan. 3, 2023, 4 pages.
Patent Owner's Updated Exhibit List as of Jan. 3, 2023 for Case IPR2022-00617, dated Jan. 3, 2023, 9 pages.
Order of Termination due to Settlement After Institution of Trial and Granting Joint Request to Treat Settlement Agreement as Business Confidential Information under 35 U.S.C. § 317 and 37 C.F.R. § 42.74 in Case IPR2022-00617, dated Jan. 25, 2023, 4 pages.

* cited by examiner

PROTOCOL FOR TREATMENT OF LUPUS NEPHRITIS

CROSS-REFERENCE TO RELATED APPLICATIONS

This application is a continuation of U.S. Ser. No. 16/374,701 filed 3 Apr. 2019, which is a continuation-in-part of and claims priority from U.S. Ser. No. 15/835,219, now issued as U.S. Pat. No. 10,286,036, filed 7 Dec. 2017 and which claims benefit under 35 U.S.C. Section 119(e) of U.S. Provisional Patent Application Nos. 62/505,734, filed 12 May 2017, and 62/541,612, filed 4 Aug. 2017. The contents of the above patent applications are incorporated by reference herein in their entirety.

TECHNICAL FIELD

The invention relates to treatment of lupus nephritis and other proteinuric kidney diseases with voclosorin. More specifically it relates to pharmacodynamic dosing of subjects in accordance with an improved protocol for treatment.

BACKGROUND ART

Lupus nephritis (LN) one of a number of proteinuric kidney diseases wherein an inflammation of the kidneys is caused by systemic lupus erythematosus (SLE) whereby up to 60% of SLE patients develop LN. LN is a debilitating and costly disease often leading to renal failure which requires dialysis, or renal transplant and often results in death. Indeed, patients with renal failure have an over 60-fold increased risk of premature death compared to SLE patients in general. A clinical sign of LN is leakage of blood proteins into the urine and the disease can be diagnosed by a number of factors, including urinary protein/creatinine ratio (UPCR) wherein a UPCR of greater than 0.5 mg/mg is indicative of the condition being in an active state. Further, certain markers in the blood can also be diagnostic—for example, complement 3 (C3), complement 4 (C4) and anti-dsDNA antibodies.

The standard of care for LN has not met with a great deal of success. The standard of care is use of mycophenolate mofetil (MMF) or intravenous cyclophosphamide. With these treatments partial remission was found only in approximately 50% of cases and complete remission was shown in less than 10% of the subjects. Thus, there is clearly a need for a treatment that improves these outcomes.

Voclosporin is an analog of cyclosporin A that has been found useful for treating autoimmune diseases and as an immunosuppressant in organ transplantation.

Mixtures of the E and Z isomers of voclosporin are described in U.S. Pat. No. 6,998,385. Mixtures with a preponderance of the E-isomer are described in U.S. Pat. No. 7,332,472. The '472 patent describes a number of indications which can be treated with the isomeric voclosporin mixture including glomerulonephritis. However, although some animal studies are described, no protocols in humans are disclosed.

Various formulations of voclosporin mixtures are also described in U.S. Pat. Nos. 7,060,672; 7,429,562 and 7,829,533.

In October 2016, the results of a clinical study conducted on behalf of Aurinia Pharmaceuticals were published as an abstract. According to the abstract, the subjects, who were afflicted with lupus nephritis (LN), were dosed with 23.7 mg of voclosporin twice daily in combination with mycophenolate mofetil (MMF) and reducing cortical steroid dose over 24 weeks for which data were presented. Entry criteria for the study included determination of a urine protein creatinine ratio (UPCR) of ≥1.0 mg/mg or ≥1.5 mg/mg depending on the classification of a renal biopsy and an eGFR (estimated glomerular filtration rate) of ≥45 mol/mn/ 1.73 $m^2$ as well as serologic evidence of LN. The results of this protocol showed complete remission or partial remission in a large percentage of subjects.

In addition, it was shown that subjects who achieved a ≥25% reduction in UPCR at 8 weeks were likely to maintain benefit throughout the 24-week or 48 week protocol.

In a news release sent by Aurinia Pharmaceuticals on 1 Mar. 2017, the results of more extensive clinical study involving mycophenolate mofetil (MMF) and reducing corticosterone dosages, but using in addition to 23.7 mg of voclosporin twice daily, a higher dose of 39.5 mg twice daily were described. The results of this study showed successful complete or partial remission in a large number of patients at 24 weeks and 48 weeks. It appeared that the lower dosage of 23.7 mg twice daily (BID) was even more effective than the higher dosage of 39.5 mg twice daily (BID).

Data regarding predictability of success with respect to complete remission (CR) based on various criteria measured after 8 weeks of treatment with 23.7 bid of Voclosporin along with MMF-1 and steroid taper were presented by the present inventors at the $12^{th}$ International Congress on SLE on 27 Mar. 2017. These criteria included UPCR (less than 25% reduction considered to show ineffectiveness) as well as normalization of complements 3 and 4 (C3 and C4) and of anti-dsDNA. However, the criteria for normalization of C3, C4 and anti-dsDNA were not disclosed.

An earlier study with respect to lupus treatment with cyclophosphamide rather than Voclosporin suggested normalization of C4 as a marker. Dall'Era, M. et al Arth. Care and Res. (2011) 63:351-357.

It has now been found that successful results, including a diminution in the number and severity of side effects can be obtained by altering the protocols disclosed in these publications by providing a pharmacodynamic dosing schedule based on individual patient responses. In addition, it has been found that even lower dosages of voclosporing—i.e., 15.8 mg of voclosporin twice daily or 7.9 mg of voclosporin twice daily are effective.

DISCLOSURE OF THE INVENTION

The present invention, thus, provides an improved protocol for treatment of lupus nephritis and other proteinuric kidney diseases that takes advantage of assessments of parameters associated with the response of individual subjects. The invention is a personalized form of a protocol for treatment of proteinuric kidney diseases including protocols that employ low dosage of voclosporin. The voclosporin used is preferably a mixture of greater than about 80% E isomer and less than about 20% Z isomer, and more preferably greater than about 90% E isomer and less than about 10% Z isomer. The protocol employs daily dosages of voclosporin over a projected period of 24, 48, 52 weeks or longer wherein the voclosporin is administered twice daily (BID). Suitable dosages are in increments of 7.9 mg including 39.5 mg, 31.6 mg, 23.7 mg, 15.8 mg or 7.9 mg. Low dosages show superior results compared to a higher dose of 39.5 mg each of such aministrations carried out twice daily. Doses as low as 15.8 mg or 7.9 mg twice daily are effective. The protocol preferably further includes administering to the subject an effective amount of MMF and/or an effective amount of a corticosteroid, typically prednisone, in a reducing dosage level across the time period of the study.

While it has been verified that the protocols of the invention are effective for lupus nephritis, such results indicate the same protocols can be used to generally treat proteinuric kidney diseases. Proteinuric kidney diseases that can be treated include: Diabetic nephropathy, nephrotic syndromes (i.e. intrinsic renal failure), nephritic syndromes, toxic lesions of kidneys, glomerular diseases, such as membranous glomerulonephritis, focal segmental glomerulosclerosis (FSGS), IgA nephropathy (i.e., Berger's disease), IgM nephropathy, membranoproliferative glomerulonephritis, membranous nephropathy, minimal change disease, hypertensive nephrosclerosis and interstitial nephritis.

One of the side effects of treatment with voclosporin is an unwanted decrease in the estimated glomerular filtration rate (eGFR). One invention protocol is designed to reduce the incidence of this undesirable side effect by adjusting the dosage in accordance with the response of the subject.

Thus, in one aspect, the invention is directed to a pharmacodynamic method to treat a proteinuric kidney disease which method comprises administering to a subject diagnosed with said disease a predetermined daily dosage of effective amounts of voclosporin over a projected treatment period of at least 24 weeks, said pharmacodynamic method further comprising:

(a) assessing the estimated Glomerular Filtration Rate (eGFR) of said subject at at least a first time point and a second time point on different days of said treatment period, and (b) (i) if the eGFR of said subject decreases by more than a target % to below a predetermined value between said first and second time points, reducing the daily dosage by increment(s) of 7.9 mg BID or stopping the administering of voclosporin to said subject;

(ii) if the eGFR of said subject decreases by less than said target % between said first and second time points, continuing administering the same predetermined daily dosage of voclosporin to said subject.

In one specific embodiment, the invention includes a pharmacodynamic method to treat lupus nephritis which method comprises administering to a subject diagnosed with lupus nephritis a predetermined daily dosage of effective amounts of voclosporin over a projected treatment period of at least 24 weeks, said pharmacodynamic method further comprising:

(a) assessing the glomerular filtration rate (eGFR) of said subject at at least a first time point and a second time point on different days of said treatment period, and (b) (i) if the eGFR of said subject decreases by ≥30% to a value of below 60 mL/min/1.73 m² between said first and second time points, stopping the administering of voclosporin to said subject;

(ii) if the eGFR of said subject decreases by between 20% to 30% to a value of below 60 ml/min/1.73 m² between said first and second time points, administering a reduced dosage of voclosporin to said subject;

(iii) if the eGFR of said subject decreases by ≤20% between said first and second time points, continuing administering the same predetermined daily dosage of voclosporin to said subject.

The eGFR of 60 mL/min/1.73 m² noted above is typically used; however, higher values such as 90 mL/min/1.73 m² or 75 or 70 mL/min/1.73 m² or lower value such as 50 mL/min/1.73 m² or 55 mL/min/1.73 m² could also be used.

The pharmacodynamic method may employ a third time point subsequent to the first and second time point wherein the target percentage reduction is again determined and if the percentage reduction as compared to the first time point is less than the target percentage, treatment may be restored, or if the percentage decrease is greater than the target percentage exhibited at the second time point, further reduction in dosage may be indicated.

A second embodiment relates to using blood pressure as an indicator rather than eGFR. In this second embodiment, the invention is directed to a pharmacodynamic method to treat lupus nephritis which method comprises administering to a subject diagnosed with lupus nephritis predetermined daily dosages of effective amounts of voclosporin over a projected treatment period of at least 24 weeks, said pharmacodynamic method further comprising:

(a) measuring the blood pressure (BP) of said subject at at least a first time point of said treatment period; and (b) stopping the administering of voclosporin to the subject or administering a reduced dosage of voclosporin to said subject if either value of the cystolic or diastolic component of the BP of said subject is >130/80.

In this case, an additional time point measuring BP may be employed and if both components of the BP of the subject are below 130/80, the administration of the predetermined daily dose of voclosporin may be resumed.

Thus, blood measure elevation is an additional undesirable side-effect of treatment that can be used as a criterion for adjusting dosage.

It has also been found that the effectiveness of the protocol can be evaluated after only a portion of the treatment period has elapsed. This can be done in lieu of, or in addition to, the foregoing protocol. Therefore, because it is generally undesirable to continue an ineffective treatment an assessment at a time point earlier in the protocol than the end point planned is conducted and if the effectiveness of treatment is not confirmed, the treatment is terminated. In the present case, such termination may be helpful since generally administration of an immunosuppressant is not recommended unless some benefit is achieved.

For example, the assessment may include determining the UPCR at first and second time points early in the protocol wherein the first point is determined at the outset of the protocol and stopping the administration of voclosporin to the subject if the UPCR has not been reduced by a predetermined amount, for example by 15% or 20% or 25% or 35% at the second time point. The UPCR can be determined by any standard technique, e.g., using first morning void or a 24 hour urine sample. This evaluation may be supplemented or substituted by evaluation of the concentration of C3 and C4 in the blood. Failure of the treatment to result in normalizing C3/C4 concentration indicates lack of success. The rule for stopping treatment if a combination of these factors is employed is that treatment will be stopped if neither criterion for success is met—i.e. the subject shows no satisfactory reduction in UPCR at the second time point and no normalization of C3/C4 at the second time point. In the alternative, either criterion could be used alone.

Alternatively, if it appears that the subject is in complete remission, it may be unnecessary to continue treatment.

In any of the protocols above, preferably, a dosage of MMF and a reducing dosage of corticosteroid is also administered during the treatment period. Typically, MMF is administered at the level of 2 grams daily and oral corticosteroids are administered in daily dosages diminishing from 20-25 mg daily to 2.5 mg daily over a period of 16 weeks. The reduced dosages then continue throughout the study. These protocols are shown in FIG. 1.

In all cases, subjects who would be amenable to this treatment are identified by screening said subject prior to conducting said method on said subject by:

(a) determining that the urine protein creatinine ratio (UPCR) of said subject is ≥1.5 mg/mg or ≥1 mg/mg depending on renal biopsy as preferably measured by first morning void; and (b) determining said subject has an eGFR as measured by the Chronic Kidney Disease Epidemiology Collaboration equation (CKD-EPI) of ≥45 mL/min/1.73 m² or any other suitable method such as the Modification of Diet in Renal Disease (MDRD) Study equation. If the determinations of subparagraphs (a) and (b) are positive, the subject is considered suitable for subjection to the protocol.

In addition, lowered levels of voclosporin dosage have been shown to be effective.

Thus, in another aspect, the invention is directed to a method to treat lupus nephritis which method comprises administering to a subject diagnosed with lupus nephritis a predetermined daily dosage of effective amounts of voclosporin wherein said effective amount is either 15.8 mg BID or 7.9 mg BID. Surprisingly, it has been found that these lower dosages are effective in a majority of patients, especially if the treatment is prolonged beyond 24 weeks. A dosage of 31.6 mg BID (4 capsules) could also be employed. Pharmacodynamic dosing can be applied in these instances as well.

It is also advantageous and part of the invention to evaluate a subject who has been treated with the protocol at the end of the treatment period to determine whether a complete or partial remission has occurred. Further evaluations are included at a time subsequent to termination of the treatment to assess whether the remission achieved according to the measurement at the end of the treatment is being maintained. Such evaluation may also be done at intermediate times during treatment to determine whether dosage can be reduced. In an exemplary embodiment used simply for illustration a dosage of 23.6 mg voclosporin BID may be reduced to 15.8 mg or 7.9 mg BID based on such results.

The evaluation for effectiveness can be based on the protein/creatinine ratio in urine (UPCR) where a ratio of ≤0.5 mg/mg indicates complete response; alternatively, or in addition, an eGFR of ≥60 mL/min/1.73 m² or no decrease from baseline and eGFR of ≥20% is shown. Other indications of complete response include lack of need for rescue medications such as intravenous steroids, cyclophosphamide or a need for ≤10 mg prednisone for more than three consecutive days or more than seven days total. These evaluations may be performed at any point in the treatment.

MODES OF CARRYING OUT THE INVENTION

Figure 1:
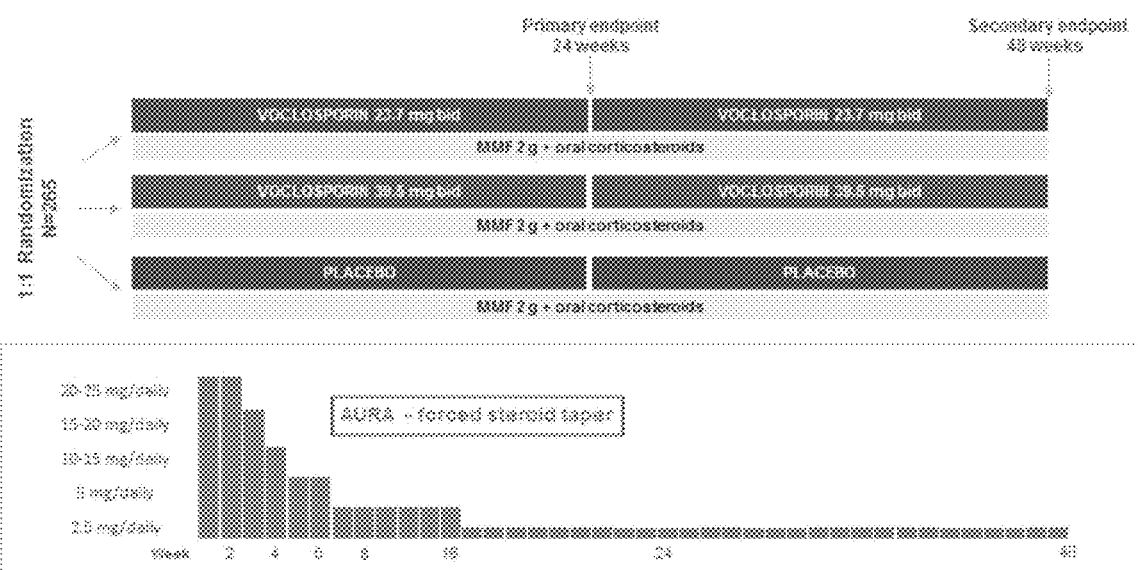
FIG. 1 shows graphically the design of a protocol for treatment of lupus nephritis with voclosporin upon which the pharmacodynamic treatment of the invention is superimposed.

As noted above, the pharmacodynamic protocol of the invention relates to adjustment of administration of voclosporin depending on certain physiological indicators of the subjects. As further noted, the voclosporin administration is preferably conducted with a background of administration of MMF and of corticosteroids.

In general, the treatment protocols on which the invention is based show dramatically better results than the current standard of care—the rate of complete remission is almost 50% as compared to much lower levels achieved using the current standard of care treatment and the rate of partial remission after 48 weeks is even higher, wherein this rate (PR) includes the subjects with complete remission (CR). As shown below, a lower dosage of voclosporin is more effective than a higher dose in a comparable protocol wherein complete remission was obtained in 40% of the subjects at the higher dosage as opposed to 49% of the subjects in the lower dose group.

Critical to the present invention is pharmacodynamic administration of the voclosporin component. This pharmacodynamic administration is essential as the effects of this drug may be too intense and/or have undesirable side effects or the results may indicate lack of effectiveness and thus the dosage is reduced or interrupted to permit homeostasis to reestablish a suitable set of physiological parameters.

The protocols are designed to cover treatment periods of at least 24 weeks and may extend for longer periods of time, for example 48 weeks or 52 weeks. The regimens involve daily dosages of the voclosporin component, typically twice daily, although alternative frequencies could be employed, such as once a day, three times a day or four times a day based on reactions of the patient and convenience. As an illustration, the protocol will be described below in terms of a 23.7 mg twice daily (BID) dosage; of course if the voclosporin preparation is administered four times daily, the dosage would be cut in half for each administration and if the administration were only once per day, the dosage for the once a day administration would be double the 23.7 mg administered BID.

In addition, as to the pharmacodynamic protocols of the invention, the dosages may be any combination of the 7.9 mg basic units, and thus can be 7.9 mg, 15.8 mg, 31.6 mg, or 39.5 mg, as well as the exemplified 23.7 mg.

The dosage indicated, for example 23.7 mg, (or any other specified dose) is subject to slight variations, typically ±10% or, alternatively, for 23.7 mg specified between 21 mg and 26 mg BID. This is due to inconsistencies in pharmaceutical manufacture and the ideal dosage is the specified dose—i.e., for example, 23.7 mg BID. Comparable variations applied to the alternative dosages, and to the differential adjustment.

Adjustment Based on eGFR:

One critical parameter used to assess the desirability of dosage reduction is the eGFR using the CKD-EP1 formula or other appropriate method. Chronic kidney disease is defined as eGFR as ≤60 mL/min/1.73 m² for ≥three months with or without kidney damage. As noted above, a further decrease in eGFR is a negative side effect that may occur during treatment. If the decrease is too severe, the protocol should be altered in accordance with the prescription of the invention. Typically, a baseline value of the eGFR is established either at the beginning of the protocol or at some "first time point" during the protocol. If the decrease is greater than a target percentage, which is typically between 20%-45% as compared to the first time point, a reduction in dosage is indicated, including a reduction to zero or stopping treatment. If the decrease is less than that target percentage maintenance of treatment at the same level as indicated. In addition to an indication that treatment should be reduced or terminated based on the eGFR reduction, reduction below a certain value is also indicative of a need to modify the treatment. This predetermined value is typically in the range of 50-90 mL/min/1.73 m$^2$.

As stated above, a baseline value for eGFR is established at the outset of the treatment or during treatment. This is typically done on the first day of the treatment before any administration of the drugs in the protocol. This baseline is used as a criterion for adjusting dosage. However, a first time point could be established at any arbitrarily selected time during the protocol.

In one exemplary protocol, at a second time point subsequent to the first which can be on any day of the treatment, a subject with ≥30% decrease in eGFR from the baseline to <60 ml/min/1.73 m$^2$ (or, in some cases, a higher cut off) should have the treatment interrupted until a repeat test can be performed, but if the decrease is confirmed and not due to contributing factors (such as a high baseline eGFR, the addition or modification of non-steroidal anti-inflammatory drugs, angiotensin converting enzyme inhibitors, angiotensin 2 inhibitor blockers, or a concurrent state of dehydration, etc.), the treatment should be withheld until a third time point determination typically within 48 hours. If the ≥30% decrease is not maintained, treatment is restored to two-thirds or one-third of the original dosage and increased as tolerated to the 23.7 mg level BID.

For convenience, the 23.7 mg administration is administered orally in the form of three capsules containing 7.9 mg each. Thus, it is easy to provide two-thirds of the standard dosage by administering at any given time only two of the three capsules.

With regard to the second time point, in this exemplary protocol a subject having a decrease of ≥20% in eGFR to ≤60 mL/min/1.73 m$^2$ but a decrease of less than 30% reduction as compared to baseline, the treatment is not interrupted but the dosage is reduced. Reduction in increments of 7.9 mg is preferred. Again, assessment at an additional time point at any subsequent day during the treatment showing baseline values are restored indicates that the original dosage level of 23.7 mg BID can be resumed.

Adjustment Based on Blood Pressure

An alternative parameter that can be used to determine pharmacodynamic dosage is blood pressure. As voclosporin may increase blood pressure to undesirable levels, at any point during the treatment period if either component of the blood pressure i.e. the cystolic or diastolic pressure of the subject is ≥130/80, the treatment should be reduced, preferably by increments of 7.9 mg. At a later time point if both components of the blood pressure are below 130/80, the treatment can be restored to the original level.

Adjustment Based on UPCR Reduction and/or C3/C4 Normalization

Suitable criteria for early evaluation of the probability of success—i.e. complete or partial remission by the end of a planned protocol, have been identified which permit discontinuation of the treatment earlier than the end point if it is highly unlikely that the subject will benefit from continuing on the dosage schedule. These criteria are reduction in UPCR and normalization of C3/C4. These can be used in combination or in the alternative. It has been found that a determination early in a 24-week or 48 week protocol of probable success can be used to determine whether treatment with voclosporin should continue; such findings are applicable to protocols of any substantial length. By way of illustration, if the UPCR has not been reduced by a satisfactory amount early in the regimen or if C3/C4 has not been normalized early in the regimen, one might conclude that the chances of improvement over an extended treatment period are diminished. Application of these criteria in an exemplary trial is shown in detail in Example 3.

However, a rule for stopping treatment is based either on UPCR reduction or C3/C4 normalization taken alone or in combination. If the combination is used, then failure with respect to both criteria would dictate termination of treatment. Decision would be based on the values of the sensitivity, specificity and positive and negative predictive values shown in the tables set forth in Example 3. These terms are defined in the Example.

As an illustration only, such determination can be made at approximately 8 weeks subsequent to the beginning of the regimen; a time frame of 6-10 weeks could be employed for the approximation of 8 weeks. If a decrease of, for example, ≥25% of UPCR is not achieved, it appears unlikely the subject will benefit from further treatment and the protocol is stopped. As shown in the Example, this can be supplemented with evaluation of C3/C4 normalization—if this is done, it is desirable that both determinations be made at the same early time point.

Auxiliary Therapeutics

The voclosporin treatment of the invention is supplemented with MMF and reduced amounts of corticosteroids.

For example, with respect to corticosteroids, subjects who weigh 45 kg or more may receive 0.5 grams of methylprednisolone on days 1 and 2 of the study intravenously and then beginning on day 3, oral corticosteroid therapy. Subjects weighing ≤45 kg receive only half these dosages.

For oral prednisone, the starting dosage for oral administration is 20 mg/day for subjects <45 kg and 25 mg/day for subjects who weigh ≥45 kg. The dosage is reduced according to the protocol shown in Table 1.

TABLE 1

Dosing Schedule for IV Methylprednisolone and Daily Oral Prednisone (mg)

| | Subjects <45 kg | Subjects ≥45 kg | In Case of Prior IV Steroids During Screening (Pre-randomization) |
|---|---|---|---|
| Weeks 1-2[1] | | | |
| Days 1-2[2] | 0.25 g (IV) | 0.5 g (IV) | 1 g minus prior IV steroids mg or (0.5 g minus prior IV steroids mg for subjects who weigh <45 kg)[3] |
| Days 3-13 | 20 mg (oral) | 25 mg (oral) | |
| Week 2 (Day 14) | 15 mg (oral) | 20 mg (oral) | |
| Week 4 (Day 28) | 10 mg (oral) | 15 mg (oral) | |
| Week 6 (Day 42)[4] | 10 mg (oral) | 10 mg (oral) | |

TABLE 1-continued

Dosing Schedule for IV Methylprednisolone and Daily Oral Prednisone (mg)

|  | Subjects <45 kg | Subjects ≥45 kg | In Case of Prior IV Steroids During Screening (Pre-randomization) |
|---|---|---|---|
| Week 8 (Day 56) | 5 mg (oral) | 5 mg (oral) | |
| Week 12 (Day 84) | 5 mg (oral) | 5 mg (oral) | |
| Week 16 (Day 112) | 15 mg (oral) | 2.5 mg (oral) | |

[1]Day 0-13; Oral Steroids dosed according to subject weight and then tapered beginning at Day 14.
[2]Oral corticosteroids may be commenced on Days 1 or 2 if corticosteroids are administered during screening.
[3]Its recognized that dosing with IV methyprednisolone as described in Section 7.2.2.2, Corticosteroids may not be in the subject's best interest if they have already received therapy within the 3 months prior to screening. In this case, the Investigayor may be permitted to omit the administration of further IV methylprednisolone but only after discussion with the Medical Monitor.
[4]Week 6 is not a scheduled study visit, a phone call can be performed to decide further tapering for subjects
Notes:
Oral prednisone taper should he done within ±3 days of specified timeframe. When clinically indicated, subjects are allowed to be completely titrated off of oral corticosteroids.
Abbreviation: IV = intravenous In contrast to the reducing dose of corticosteroid, the same dose of MMF is maintained throughout the study at a twice daily dosage before meals with a glass of water. Typically, each individual dose is one gram resulting in a total dosage of two grams per day although in the alternative, the subject may be administered 500 mg four times daily.

Low Dosage

In addition to the above-described pharmacodynamic protocols, applicants have found that a substantially lower dosage than expected is effective in large numbers of subjects such that a method to treat lupus nephritis in subjects either with or without pharmacodynamic adjustments can be based on a dosage level of either 15.8 mg BID or 7.9 mg BID. The increments of 7.9 mg are dictated by the availability of capsules containing the 7.9 mg dosage level which provides a convenient platform for dosage alterations.

One additional aspect of the invention is therefore a method to treat lupus nephritis wherein either a logically adjusted dosage or a constant dosage of either 15.8 mg BID or 7.9 mg BID is employed. In these protocols, as would be the case for higher dosages of voclosporin, the above described background administration of MMF and corticosteroids is included in the protocol.

General Factors

In all cases, the subjects are evaluated for success of the treatment both on the completion of the treatment and at extended periods thereafter. Typical treatment periods are at least 24 weeks, but preferably 48 weeks or more. Reevaluation after the termination of the treatment period over a period of 1-2 weeks or longer is also employed. Subjects are evaluated for complete or partial remission. Complete remission (CR) is defined as: Confirmed protein/creatinine ratio of ≤0.5 mg/mg, and eGFR ≥60 mL/min/1.73 $m^2$ or no confirmed decrease from baseline in eGFR of ≥20%. Partial remission is defined as: 50% reduction in UPCR from baseline.

By establishing a pharmacodynamic dosing regimen, the effectiveness of the protocol in treatment of lupus nephritis can be maximized while minimizing undesirable side effects.

The length of the treatment protocol in all cases will vary from at least 8 weeks to for example 12, 16, 24 and 48 weeks or 52 weeks or even longer, up to 60 weeks including stopping points between the levels mentioned. For example, a treatment protocol of 10 or 11 or 15 or 20 or 29 or 31 or 36 or 43 or 51 or 55 weeks could be employed and is within the scope of the invention. The evaluation described above is conducted at the end of the protocol as well as at a suitable time period or multiple time periods thereafter. These time periods are generally 1-2 weeks to 4-5 months subsequent to terminating the dosage and intervening at time intervals are included within the scope of the invention as well.

This statement regarding time intervals applies to the invention pharmacodynamic treatment protocols, regardless of base dosage levels.

The following examples are to illustrate, not to limit the invention.

EXAMPLE 1

48 Week Study of LN Treatment

The subjects enrolled in the study were divided into three groups, 88 subjects are in a control group who were administered 2 g MMF daily as well as oral corticosteroids—i.e., prednisone in a tapering dosage shown graphically in FIG. 1—beginning at 20-25 mg daily reduced gradually after the $12^{th}$ week to 2.5 mg daily. (Some subjects received lower doses of MMF due to gastrointestinal problems). 89 subjects in the low dosage group received this background treatment, but in addition were administered three capsules containing 7.9 mg (i.e. 23.7 mg) of voclosporin each twice daily. The voclosporin used in this study comprised greater than 90% E isomer. A third group which was comprised of 88 subjects received a similar background treatment but in addition were dosed with five 7.9 mg capsules i.e. 39.5 mg twice daily. The study was conducted over a period of 48 weeks and safety was evaluated at 24 weeks.

Subjects were screened prior to admission to the study by (a) determining that the urine protein creatinine ratio (UPCR) as >1.5 mg/mg as measured by first morning void, and (b) that the eGFR as measured by Chronic Kidney Disease Epidemiology Collaboration equation (CKD-EP1) of >45 ml/min/1.73 $m^2$. Subjects were assessed after 24 weeks and 48 weeks as well as a subsequent evaluation at 50 weeks.

Figure 2:
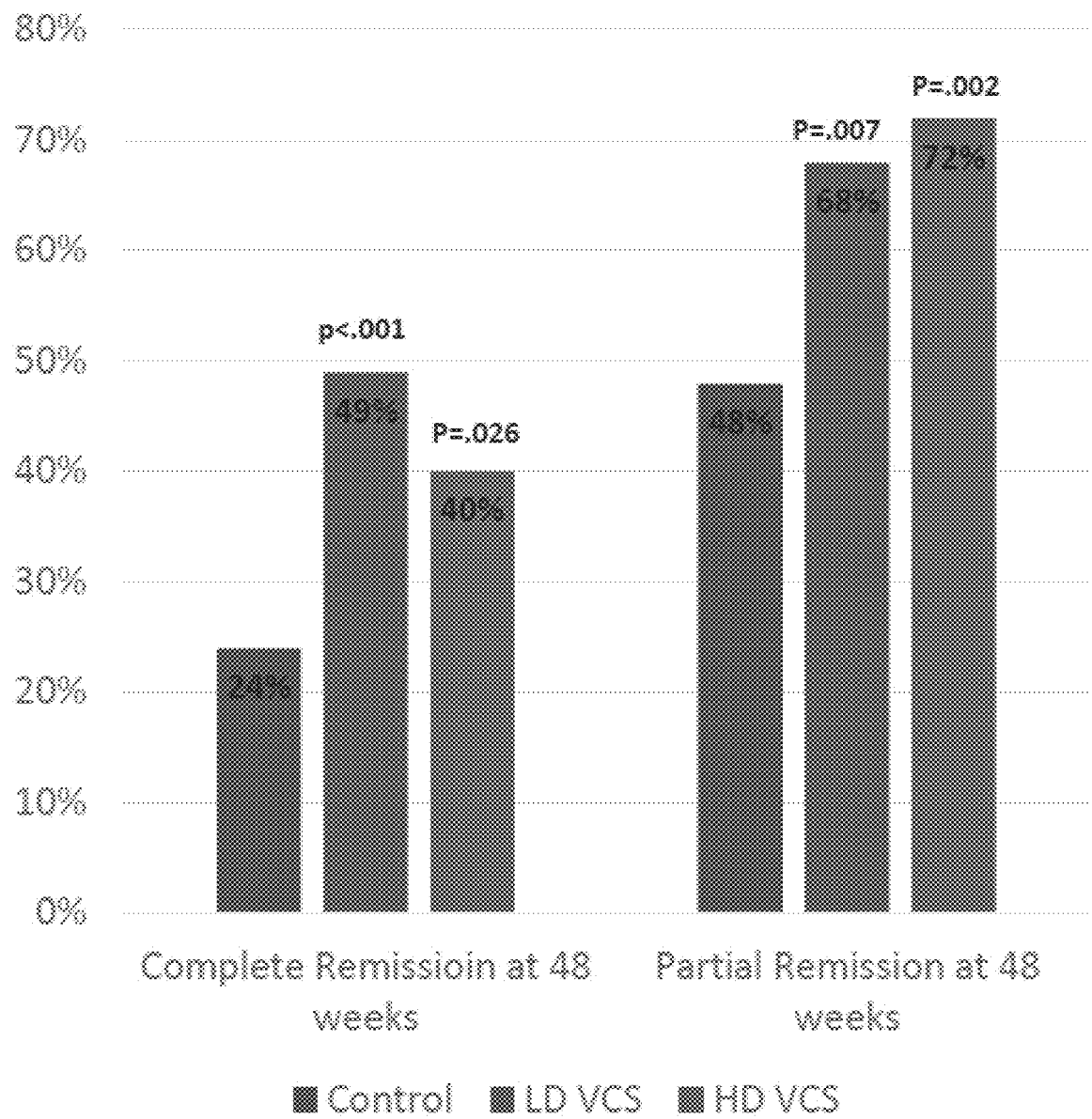
FIG. 2 is a bar graph showing a comparison of complete remission (CR) at 48 weeks and partial remission (PR) at 48 weeks for low dose as compared to high dose of voclosporin (VCS). The PR percentages include the CR percentages.

As shown in FIG. 2, the low dosage administration achieved better results than administration of voclosporin at higher dosages. After 48 weeks of treatment, 49% of low dosage subjects showed complete remission at 48 weeks, compared to 40% of high dosage subjects. In the same study, but after 24 weeks of treatment, 32.6% of low dosage patients, but only 27% of high dosage patients showed complete remission (CR) compared to 19.3% of controls. At 24 weeks, 70% of low dosage patients and 66% of high dosage patients showed partial remission (PR) compared to 49% of controls.

CR in this example is a composite end-point which includes efficacy, safety and low-dose steroids: UPCR ≤0.5 mg/mg (confirmed); eGFR >60 ml/min/1.73 m2 or within 20% of baseline; steroids ≤10 mg/day; no administration of rescue medication.

PR is a composite end-point that includes safety and efficacy: UPCR reduction of 50% from baseline and no use of rescue medication To determine the efficacy of the pharmacodynamic protocol wherein dosage is reduced or stopped according to the presence or absence of indicators of the decrease in eGFR experienced as a side effect, these three groups of patients were assessed after 24 weeks and 48 weeks of treatment with respect to whether treatment was altered according to the invention protocol. In all three groups, the patients were evaluated according to the criteria set forth in the exemplary protocol above—i.e., wherein the eGFR of each patient was measured immediately prior to administering the first dose of voclosporin and at a second time point at least a day later and (i) if the eGFR of said subject decreased by ≥30% to a value of below 60 mL/min/1.73 m$^2$ between said first and second time points, stopping the administering of Voclosporin or reducing dosage thereof to said subject;

(ii) if the eGFR of said subject decreased by between 20% to 30% to a value of below 60 ml/min/1.73 m$^2$ between said first and second time points, administering a reduced dosage of voclosporin to said subject;

(iii) if the eGFR of said subject decreased by ≤20% between said first and second time points, continuing administering the same predetermined daily dosage of voclosporin to said subject.

The results are shown in Tables 2 and 3 below. Table 2 shows percentages with complete remission (CR) or partial remission (PR) after 24 weeks and Table 3 shows these values after 48 weeks for patients that had no dose reduction and those who did have dose reduction.

TABLE 2

Patients with a No Dose Reductions (24 weeks):

| Group | Patient number (n) | Patients with no Dose Reduction n(%) | Patients with CR at 24 weeks n(%) | Patients with PR at 24 weeks n(%) |
|---|---|---|---|---|
| Placebo | 88 | 77 (87.5) | 14 (18.2) | 36 (46.8) |
| Low Dose | 89 | 50 (56.2) | 15 (30.0) | 34 (68.0) |
| High Dose | 88 | 41 (46.6) | 11 (26.8) | 24 (58.5) |

Patients with Dose Reductions (pharmacodynamically dosed):

| Group | Patient number (n) | Patients with Dose Reduction n(%) | Patients with CR at 24 weeks n(%) | Patients with PR at 24 weeks n(%) |
|---|---|---|---|---|
| Placebo | 88 | 11 (12.5) | 3 (27.3) | 7 (63.6) |
| Low Dose | 89 | 39 (43.8) | 14 (35.9) | 28 (71.8) |
| High Dose | 88 | 47 (53.4) | 13 (27.7) | 34 (72.3) |

TABLE 3

Patients with No Dose Reductions (48 weeks):

| Group | Patient number (n) | Patients with no Dose Reduction n(%) | Patients with CR at 48 weeks n(%) | Patients with PR at 48 weeks n(%) |
|---|---|---|---|---|
| Placebo | 88 | 74 (84.1) | 18 (24.3) | 38 (51.4) |
| Low Dose | 89 | 43 (48.3) | 20 (46.5) | 26 (60.5) |
| High Dose | 88 | 35 (39.8) | 11 (31.4) | 22 (62.9) |

Patients with Dose Reductions (pharmacodynamically dosed):

| Group | Patient number (n) | Patients with Dose Reduction n(%) | Patients with CR at 48 weeks n(%) | Patients with PR at 48 weeks n(%) |
|---|---|---|---|---|
| Placebo | 88 | 14 (15.9) | 3 (21.4) | 4 (28.6) |
| Low Dose | 89 | 46 (51.7) | 24 (52.2) | 35 (76.1) |
| High Dose | 88 | 53 (60.2) | 24 (45.3) | 41 (77.4) |

In this study, CR was defined as a composite of UPCR ≤0.5 mg/mg; eGFR >60 mL/min/1.73 m$^2$ or within 20% of baseline, steroids at ≤10 mg/day and no administration of rescue medication. PR is defined as UPCR reduction of 50% from baseline and no use of rescue medication.

As shown in Table 2, 12.5% of patients on placebo, 43.8% of patients on low dose and 53.4% of patients on high dose voclosporin underwent dose reduction during the treatment. The percentage of patients with complete response after 24 weeks was not affected in either dosage groups by the pharmacodynamic dosage and the percentage with partial response was also roughly the same, although with the high dose group, the percentage with partial reduction improved. Table 3 shows similar results at 48 weeks, although a higher percentage of patients were subjected to dose reduction. Again, no drastic effect on the overall response was exhibited.

EXAMPLE 2

Low Dosage Protocol

In the course of clinical studies similar to those in Example 1, it was observed that a substantial portion of subjects showed substantial remission at a dosage reduced almost immediately to 15.8 mg voclosporin administered twice daily (BID). Accordingly, applicants have analyzed these data and have concluded that a dosage protocol providing 15.8 mg or 7.9 mg voclosporin BID is effective with or without the pharmacodynamic aspects of the protocol.

As the capsules contain 7.9 mg voclosporin, 1 cap represents 7.9 mg voclosporin, 2 caps represent 15.8 mg voclosporin and 3 caps represent 23.7 mg voclosporin, etc. Substantial numbers of subjects showed complete or partial remission even when the dosage was lowered to 7.9 mg voclosporin BID quite early in the treatment and similar results were obtained for administration of 15.8 mg BID.

EXAMPLE 3

Predictability Based on Early Responses

In the study reported in Example 1, the predictability of outcomes based on markers at early time points were determined. These results are shown in Tables 4-12.

In the study described in Example 1, data were obtained to ascertain whether markers evaluated after various time-points during treatment would predict an ultimate favorable outcome or show that continuing treatment was likely to be futile. This is important because it is undesirable to subject a patient to unnecessary treatment, even if the treatment is relatively safe. These data are shown in the tables below.

Based on these data, the sensitivity and specificity of the evaluation of each marker and their counterparts positive predictive value and negative predictive value were determined with respect to whether the patient would or would not show partial remission (PR) after 48 weeks of the treatment protocol. PR is defined as at least 50% reduction in proteinuria (i.e. UPCR). This would also include subjects who showed complete remission (CR).

Sensitivity is defined as the probability that a subject showing PR at 48 weeks would have shown a favorable result with regard to the marker at the designated early time point. In the tables below, this is the ratio of the number of subjects with favorable marker results (early drop or normalization) to the total subjects with 48 week PR.

Specificity is defined as the probability that a subject not showing PR at 48 weeks would have shown an unfavorable result with regard to the marker at the designated early time point. In the tables below, this is the ratio of the number of subjects with unfavorable marker results (no early drop or no normalization) to the total subjects with no 48 week PR.

Positive predictive value is defined as the probability that a subject showing a favorable result with respect to the marker at an earlier time point would show PR at 48 weeks. In the tables below, this is the ratio of the number of subjects with favorable marker results who have 48 week PR to those with favorable marker results (early reduction or yes column).

Negative predictive value is defined as the probability that a subject showing an unfavorable result with respect to the marker at an earlier time point would not show PR at 48 weeks. In the tables below, this is the ratio of the number of subjects with unfavorable marker results who have no PR at 48 weeks to the total subjects with unfavorable marker results (no early reduction or no column).

An ideal marker would show a value of 100 for all of these, but this is generally unattainable. As high as possible value is desirable.

Based on the results in these tables, the protocol will be designed to stop treatment at an earlier time point when the parameters set forth above are the most favorable, but at a reasonable time before the 48 week end point. (Obviously the closer to the end point, the more favorable the indicators become, but the advantage to stopping treatment is correspondingly reduced).

TABLE 4

Table 4 - Early 15% reduction in UPCR

| Week | Treatment Group | Week 48 Partial Remission | | No Week 48 Partial Remission | | Early Reduction | | Sensitivity | Specificity | Positive Predictive Value | Negative Predictive Value |
|---|---|---|---|---|---|---|---|---|---|---|---|
| | | Early Drop | No Early Drop | Early Drop | No Early Drop | Yes | No | | | | |
| 2 | Placebo | 27 | 15 | 19 | 25 | 46 | 40 | 64.3 | 56.8 | 58.7 | 62.5 |
| | Voclosporin 23.7 mg BID | 45 | 16 | 10 | 14 | 55 | 30 | 73.8 | 58.3 | 81.8 | 46.7 |
| | Voclosporin 39.5 mg BID | 39 | 21 | 15 | 9 | 54 | 30 | 65.0 | 37.5 | 72.2 | 30.0 |
| 4 | Placebo | 36 | 5 | 18 | 23 | 54 | 28 | 87.8 | 56.1 | 66.7 | 82.1 |
| | Voclosporin 23.7 mg BID | 50 | 9 | 12 | 11 | 62 | 20 | 84.7 | 47.8 | 80.6 | 55.0 |
| | Voclosporin 39.5 mg BID | 49 | 12 | 16 | 5 | 65 | 17 | 80.3 | 23.8 | 75.4 | 29.4 |
| 6 | Placebo | 35 | 7 | 22 | 17 | 57 | 24 | 83.3 | 43.6 | 61.4 | 70.8 |
| | Voclosporin 23.7 mg BID | 53 | 6 | 12 | 6 | 65 | 12 | 89.8 | 33.3 | 81.5 | 50.0 |
| | Voclosporin 39.5 mg BID | 53 | 10 | 16 | 4 | 69 | 14 | 84.1 | 20.0 | 76.8 | 28.6 |
| 8 | Placebo | 38 | 4 | 22 | 18 | 60 | 22 | 90.5 | 45.0 | 63.3 | 81.8 |
| | Voclosporin 23.7 mg BID | 55 | 5 | 12 | 7 | 67 | 12 | 91.7 | 36.8 | 82.1 | 58.3 |
| | Voclosporin 39.5 mg BID | 56 | 5 | 17 | 4 | 73 | 9 | 91.8 | 19.0 | 76.7 | 44.4 |
| 12 | Placebo | 39 | 3 | 19 | 21 | 58 | 24 | 92.9 | 52.5 | 67.2 | 87.5 |
| | Voclosporin 23.7 mg BID | 59 | 2 | 15 | 4 | 74 | 6 | 96.7 | 21.1 | 79.7 | 66.7 |
| | Voclosporin 39.5 mg BID | 57 | 5 | 14 | 4 | 71 | 9 | 91.9 | 22.2 | 80.3 | 44.4 |
| 16 | Placebo | 39 | 3 | 19 | 20 | 58 | 23 | 92.9 | 51.3 | 67.2 | 87.0 |
| | Voclosporin 23.7 mg BID | 58 | 3 | 13 | 5 | 71 | 8 | 95.1 | 27.8 | 81.7 | 62.5 |
| | Voclosporin 39.5 mg BID | 57 | 6 | 15 | 5 | 72 | 11 | 90.5 | 25.0 | 79.2 | 45.5 |
| 20 | Placebo | 38 | 4 | 21 | 16 | 59 | 20 | 90.5 | 43.2 | 64.4 | 80.0 |
| | Voclosporin 23.7 mg BID | 60 | 0 | 13 | 3 | 73 | 3 | 100.0 | 18.8 | 82.2 | 100.0 |
| | Voclosporin 39.5 mg BID | 58 | 4 | 15 | 5 | 73 | 9 | 93.5 | 25.0 | 79.5 | 55.6 |

TABLE 4-continued

Table 4 - Early 15% reduction in UPCR

| Week | Treatment Group | Week 48 Partial Remission | | No Week 48 Partial Remission | | Early Reduction | | Sensitivity | Specificity | Positive Predictive Value | Negative Predictive Value |
|---|---|---|---|---|---|---|---|---|---|---|---|
| | | Early Drop | No Early Drop | Early Drop | No Early Drop | Yes | No | | | | |
| 24 | Placebo | 37 | 3 | 18 | 17 | 55 | 20 | 92.5 | 48.6 | 67.3 | 85.0 |
| | Voclosporin 23.7 mg BID | 60 | 0 | 12 | 2 | 72 | 2 | 100.0 | 14.3 | 83.3 | 100.0 |
| | Voclosporin 39.5 mg BID | 57 | 5 | 14 | 5 | 71 | 10 | 91.9 | 26.3 | 80.3 | 50.0 |
| 26 | Placebo | 36 | 3 | 16 | 14 | 52 | 17 | 92.3 | 46.7 | 69.2 | 82.4 |
| | Voclosporin 23.7 mg BID | 55 | 0 | 9 | 3 | 64 | 3 | 100.0 | 25.0 | 85.9 | 100.0 |
| | Voclosporin 39.5 mg BID | 61 | 0 | 12 | 4 | 73 | 4 | 100.0 | 25.0 | 83.6 | 100.0 |
| 36 | Placebo | 41 | 1 | 18 | 13 | 59 | 14 | 97.6 | 41.9 | 69.5 | 92.9 |
| | Voclosporin 23.7 mg BID | 60 | 1 | 10 | 3 | 70 | 4 | 98.4 | 23.1 | 85.7 | 75.0 |
| | Voclosporin 39.5 mg BID | 62 | 1 | 12 | 6 | 74 | 7 | 98.4 | 33.3 | 83.8 | 85.7 |
| 48 | Placebo | 37 | 1 | 10 | 16 | 47 | 17 | 97.4 | 61.5 | 78.7 | 94.1 |
| | Voclosporin 23.7 mg BID | 58 | 0 | 9 | 2 | 67 | 2 | 100.0 | 18.2 | 86.6 | 100.0 |
| | Voclosporin 39.5 mg BID | 61 | 0 | 10 | 6 | 71 | 6 | 100.0 | 37.5 | 85.9 | 100.0 |

TABLE 5

Table 5 - Early 20% reduction in UPCR

| Week | Treatment Group | Week 48 Partial Remission | | No Week 48 Partial Remission | | Early Reduction | | Sensitivity | Specificity | Positive Predictive Value | Negative Predictive Value |
|---|---|---|---|---|---|---|---|---|---|---|---|
| | | Early Drop | No Early Drop | Early Drop | No Early Drop | Yes | No | | | | |
| 2 | Placebo | 24 | 18 | 15 | 29 | 39 | 47 | 57.1 | 65.9 | 61.5 | 61.7 |
| | Voclosporin 23.7 mg BID | 44 | 17 | 8 | 16 | 52 | 33 | 72.1 | 66.7 | 84.6 | 48.5 |
| | Voclosporin 39.5 mg BID | 36 | 24 | 14 | 10 | 50 | 34 | 60.0 | 41.7 | 72.0 | 29.4 |
| 4 | Placebo | 32 | 9 | 13 | 28 | 45 | 37 | 78.0 | 68.3 | 71.1 | 75.7 |
| | Voclosporin 23.7 mg BID | 49 | 10 | 12 | 11 | 61 | 21 | 83.1 | 47.8 | 80.3 | 52.4 |
| | Voclosporin 39.5 mg BID | 47 | 14 | 16 | 5 | 63 | 19 | 77.0 | 23.8 | 74.6 | 26.3 |
| 6 | Placebo | 34 | 8 | 22 | 17 | 56 | 25 | 81.0 | 43.6 | 60.7 | 68.0 |
| | Voclosporin 23.7 mg BID | 53 | 6 | 11 | 7 | 64 | 13 | 89.8 | 38.9 | 82.8 | 53.8 |
| | Voclosporin 39.5 mg BID | 53 | 10 | 15 | 5 | 68 | 15 | 84.1 | 25.0 | 77.9 | 33.3 |
| 8 | Placebo | 38 | 4 | 19 | 21 | 57 | 25 | 90.5 | 52.5 | 66.7 | 84.0 |
| | Voclosporin 23.7 mg BID | 55 | 5 | 11 | 8 | 66 | 13 | 91.7 | | 83.3 | 61.5 |
| | Voclosporin 39.5 mg BID | 55 | 6 | 17 | 4 | 72 | 10 | 90.2 | 19.0 | 76.4 | 40.0 |
| 12 | Placebo | 38 | 4 | 19 | 21 | 57 | 25 | 90.5 | 52.5 | 66.7 | 84.0 |
| | Voclosporin 23.7 mg BID | 59 | 2 | 14 | 5 | 73 | 7 | 96.7 | 26.3 | 80.8 | 71.4 |
| | Voclosporin 39.5 mg BID | 57 | 5 | 14 | 4 | 71 | 9 | 91.9 | 22.2 | 80.3 | 44.4 |
| 16 | Placebo | 39 | 3 | 17 | 22 | 56 | 25 | 92.9 | 56.4 | 69.6 | 88.0 |
| | Voclosporin 23.7 mg BID | 58 | 3 | 12 | 6 | 70 | 9 | 95.1 | 33.3 | 82.9 | 66.7 |
| | Voclosporin 39.5 mg BID | 57 | 6 | 15 | 5 | 72 | 11 | 90.5 | 25.0 | 79.2 | 45.5 |

TABLE 5-continued

Table 5 - Early 20% reduction in UPCR

| Week | Treatment Group | Week 48 Partial Remission | | No Week 48 Partial Remission | | Early Reduction | | Sensitivity | Specificity | Positive Predictive Value | Negative Predictive Value |
|---|---|---|---|---|---|---|---|---|---|---|---|
| | | Early Drop | No Early Drop | Early Drop | No Early Drop | Yes | No | | | | |
| 20 | Placebo | 38 | 4 | 20 | 17 | 58 | 21 | 90.5 | 45.9 | 65.5 | 81.0 |
| | Voclosporin 23.7 mg BID | 60 | 0 | 12 | 4 | 72 | 4 | 100.0 | 25.0 | 83.3 | 100.0 |
| | Voclosporin 39.5 mg BID | 58 | 4 | 15 | 5 | 73 | 9 | 93.5 | 25.0 | 79.5 | 55.6 |
| 24 | Placebo | 37 | 3 | 16 | 19 | 53 | 22 | 92.5 | 54.3 | 69.8 | 86.4 |
| | Voclosporin 23.7 mg BID | 59 | 1 | 11 | 3 | 70 | 4 | 98.3 | 21.4 | 84.3 | 75.0 |
| | Voclosporin 39.5 mg BID | 56 | 6 | 14 | 5 | 70 | 11 | 90.3 | 26.3 | 80.0 | 45.5 |
| 26 | Placebo | 36 | 3 | 15 | 15 | 51 | 18 | 92.3 | 50.0 | 70.6 | 83.3 |
| | Voclosporin 23.7 mg BID | 55 | 0 | 9 | 3 | 64 | 3 | 100.0 | 25.0 | 85.9 | 100.0 |
| | Voclosporin 39.5 mg BID | 61 | 0 | 12 | 4 | 73 | 4 | 100.0 | 25.0 | 83.6 | 100.0 |
| 36 | Placebo | 41 | 1 | 16 | 15 | 57 | 16 | 97.6 | 48.4 | 71.9 | 93.8 |
| | Voclosporin 23.7 mg BID | 60 | 1 | 10 | 3 | 70 | 4 | 98.4 | 23.1 | 85.7 | 75.0 |
| | Voclosporin 39.5 mg BID | 61 | 2 | 12 | 6 | 73 | 8 | 96.8 | 33.3 | 83.6 | 75.0 |
| 48 | Placebo | 37 | 1 | 9 | 17 | 46 | 18 | 97.4 | 65.4 | 80.4 | 94.4 |
| | Voclosporin 23.7 mg BID | 58 | 0 | 9 | 2 | 67 | 2 | 100.0 | 18.2 | 86.6 | 100.0 |
| | Voclosporin 39.5 mg BID | 61 | 0 | 10 | 6 | 71 | 6 | 100.0 | 37.5 | 85.9 | 100.0 |

TABLE 6

Table 6 - Early 25% reduction in UPCR

| Week | Treatment Group | Week 48 Partial Remission | | No Week 48 Partial Remission | | Early Reduction | | Sensitivity | Specificity | Positive Predictive Value | Negative Predictive Value |
|---|---|---|---|---|---|---|---|---|---|---|---|
| | | Early Drop | No Early Drop | Early Drop | No Early Drop | Yes | No | | | | |
| 2 | Placebo | 18 | 24 | 15 | 29 | 33 | 53 | 42.9 | 65.9 | 54.5 | 54.7 |
| | Voclosporin 23.7 mg BID | 39 | 22 | 8 | 16 | 47 | 38 | 63.9 | 66.7 | 83.0 | 42.1 |
| | Voclosporin 39.5 mg BID | 33 | 27 | 14 | 10 | 47 | 37 | 55.0 | 41.7 | 70.2 | 27.0 |
| 4 | Placebo | 30 | 11 | 11 | 30 | 41 | 41 | 73.2 | 73.2 | 73.2 | 73.2 |
| | Voclosporin 23.7 mg BID | 48 | 11 | 12 | 11 | 60 | 22 | 81.4 | 47.8 | 80.0 | 50.0 |
| | Voclosporin 39.5 mg BID | 45 | 16 | 16 | 5 | 61 | 21 | 73.8 | 23.8 | 73.8 | 23.8 |
| 6 | Placebo | 33 | 9 | 20 | 19 | 53 | 28 | 78.6 | 48.7 | 62.3 | 67.9 |
| | Voclosporin 23.7 mg BID | 51 | 8 | 10 | 8 | 61 | 16 | 86.4 | 44.4 | 83.6 | 50.0 |
| | Voclosporin 39.5 mg BID | 49 | 14 | 15 | 5 | 64 | 19 | 77.8 | 25.0 | 76.6 | 26.3 |
| 8 | Placebo | 35 | 7 | 17 | 23 | 52 | 30 | 83.3 | 57.5 | 67.3 | 76.7 |
| | Voclosporin 23.7 mg BID | 54 | 6 | 10 | 9 | 64 | 15 | 90.0 | 47.4 | 84.4 | 60.0 |
| | Voclosporin 39.5 mg BID | 55 | 6 | 17 | 4 | 72 | 10 | 90.2 | 19.0 | 76.4 | 40.0 |
| 12 | Placebo | 37 | 5 | 17 | 23 | 54 | 28 | 88.1 | 57.5 | 68.5 | 82.1 |
| | Voclosporin 23.7 mg BID | 57 | 4 | 13 | 6 | 70 | 10 | 93.4 | 31.6 | 81.4 | 60.0 |
| | Voclosporin 39.5 mg BID | 57 | 5 | 14 | 4 | 71 | 9 | 91.9 | 22.2 | 80.3 | 44.4 |

TABLE 6-continued

Table 6 - Early 25% reduction in UPCR

| Week | Treatment Group | Week 48 Partial Remission Early Drop | Week 48 Partial Remission No Early Drop | No Week 48 Partial Remission Early Drop | No Week 48 Partial Remission No Early Drop | Early Reduction Yes | Early Reduction No | Sensitivity | Specificity | Positive Predictive Value | Negative Predictive Value |
|---|---|---|---|---|---|---|---|---|---|---|---|
| 16 | Placebo | 39 | 3 | 17 | 22 | 56 | 25 | 92.9 | 56.4 | 69.6 | 88.0 |
| | Voclosporin 23.7 mg BID | 58 | 3 | 11 | 7 | 69 | 10 | 95.1 | 38.9 | 84.1 | 70.0 |
| | Voclosporin 39.5 mg BID | 56 | 7 | 14 | 6 | 70 | 13 | 88.9 | 30.0 | 80.0 | 46.2 |
| 20 | Placebo | 38 | 4 | 17 | 20 | 55 | 24 | 90.5 | 54.1 | 69.1 | 83.3 |
| | Voclosporin 23.7 mg BID | 59 | 1 | 11 | 5 | 70 | 6 | 98.3 | 31.3 | 84.3 | 83.3 |
| | Voclosporin 39.5 mg BID | 58 | 4 | 15 | 5 | 73 | 9 | 93.5 | 25.0 | 79.5 | 55.6 |
| 24 | Placebo | 37 | 3 | 13 | 22 | 50 | 25 | 92.5 | 62.9 | 74.0 | 88.0 |
| | Voclosporin 23.7 mg BID | 59 | 1 | 11 | 3 | 70 | 4 | 98.3 | 21.4 | 84.3 | 75.0 |
| | Voclosporin 39.5 mg BID | 55 | 7 | 12 | 7 | 67 | 14 | 88.7 | 36.8 | 82.1 | 50.0 |
| 26 | Placebo | 36 | 3 | 14 | 16 | 50 | 19 | 92.3 | 53.3 | 72.0 | 84.2 |
| | Voclosporin 23.7 mg BID | 55 | 0 | 8 | 4 | 63 | 4 | 100.0 | 33.3 | 87.3 | 100.0 |
| | Voclosporin 39.5 mg BID | 60 | 1 | 12 | 4 | 72 | 5 | 98.4 | 25.0 | 83.3 | 80.0 |
| 36 | Placebo | 41 | 1 | 16 | 15 | 57 | 16 | 97.6 | 48.4 | 71.9 | 93.8 |
| | Voclosporin 23.7 mg BID | 60 | 1 | 10 | 3 | 70 | 4 | 98.4 | 23.1 | 85.7 | 75.0 |
| | Voclosporin 39.5 mg BID | 61 | 2 | 12 | 6 | 73 | 8 | 96.8 | 33.3 | 83.6 | 75.0 |
| 48 | Placebo | 37 | 1 | 9 | 17 | 46 | 18 | 97.4 | 65.4 | 80.4 | 94.4 |
| | Voclosporin 23.7 mg BID | 58 | 0 | 9 | 2 | 67 | 2 | 100.0 | 18.2 | 86.6 | 100.0 |
| | Voclosporin 39.5 mg BID | 61 | 0 | 7 | 9 | 68 | 9 | 100.0 | 56.3 | 89.7 | 100.0 |

TABLE 7

Table 7 - Early 30% reduction in UPCR

| Week | Treatment Group | Week 48 Partial Remission Early Drop | Week 48 Partial Remission No Early Drop | No Week 48 Partial Remission Early Drop | No Week 48 Partial Remission No Early Drop | Early Reduction Yes | Early Reduction No | Sensitivity | Specificity | Positive Predictive Value | Negative Predictive Value |
|---|---|---|---|---|---|---|---|---|---|---|---|
| 2 | Placebo | 14 | 28 | 13 | 31 | 27 | 59 | 33.3 | 70.5 | 51.9 | 52.5 |
| | Voclosporin 23.7 mg BID | 37 | 24 | 6 | 18 | 43 | 42 | 60.7 | 75.0 | 86.0 | 42.9 |
| | Voclosporin 39.5 mg BID | 31 | 29 | 11 | 13 | 42 | 42 | 51.7 | 54.2 | 73.8 | 31.0 |
| 4 | Placebo | 27 | 14 | 10 | 31 | 37 | 45 | 65.9 | 75.6 | 73.0 | 68.9 |
| | Voclosporin 23.7 mg BID | 47 | 12 | 11 | 12 | 58 | 24 | 79.7 | 52.2 | 81.0 | 50.0 |
| | Voclosporin 39.5 mg BID | 45 | 16 | 15 | 6 | 60 | 22 | 73.8 | 28.6 | 75.0 | 27.3 |
| 6 | Placebo | 32 | 10 | 16 | 23 | 48 | 33 | 76.2 | 59.0 | 66.7 | 69.7 |
| | Voclosporin 23.7 mg BID | 49 | 10 | 10 | 8 | 59 | 18 | 83.1 | 44.4 | 83.1 | 44.4 |
| | Voclosporin 39.5 mg BID | 47 | 16 | 15 | 5 | 62 | 21 | 74.6 | 25.0 | 75.8 | 23.8 |
| 8 | Placebo | 34 | 8 | 15 | 25 | 49 | 33 | 81.0 | 62.5 | 69.4 | 75.8 |
| | Voclosporin 23.7 mg BID | 53 | 7 | 10 | 9 | 63 | 16 | 88.3 | 47.4 | 84.1 | 56.3 |
| | Voclosporin 39.5 mg BID | 54 | 7 | 17 | 4 | 71 | 11 | 88.5 | 19.0 | 76.1 | 36.4 |
| 12 | Placebo | 36 | 6 | 16 | 24 | 52 | 30 | 85.7 | 60.0 | 69.2 | 80.0 |
| | Voclosporin 23.7 mg BID | 56 | 5 | 12 | 7 | 68 | 12 | 91.8 | 36.8 | 82.4 | 58.3 |
| | Voclosporin 39.5 mg BID | 55 | 7 | 14 | 4 | 69 | 11 | 88.7 | 22.2 | 79.7 | 36.4 |

TABLE 7-continued

Table 7 - Early 30% reduction in UPCR

| Week | Treatment Group | Week 48 Partial Remission Early Drop | Week 48 Partial Remission No Early Drop | No Week 48 Partial Remission Early Drop | No Week 48 Partial Remission No Early Drop | Early Reduction Yes | Early Reduction No | Sensitivity | Specificity | Positive Predictive Value | Negative Predictive Value |
|---|---|---|---|---|---|---|---|---|---|---|---|
| 16 | Placebo | 39 | 3 | 16 | 23 | 55 | 26 | 92.9 | 59.0 | 70.9 | 88.5 |
|  | Voclosporin 23.7 mg BID | 58 | 3 | 11 | 7 | 69 | 10 | 95.1 | 38.9 | 84.1 | 70.0 |
|  | Voclosporin 39.5 mg BID | 55 | 8 | 13 | 7 | 68 | 15 | 87.3 | 35.0 | 80.9 | 46.7 |
| 20 | Placebo | 38 | 4 | 16 | 21 | 54 | 25 | 90.5 | 56.8 | 70.4 | 84.0 |
|  | Voclosporin 23.7 mg BID | 57 | 3 | 9 | 7 | 66 | 10 | 95.0 | 43.8 | 86.4 | 70.0 |
|  | Voclosporin 39.5 mg BID | 57 | 5 | 15 | 5 | 72 | 10 | 91.9 | 25.0 | 79.2 | 50.0 |
| 24 | Placebo | 37 | 3 | 11 | 24 | 48 | 27 | 92.5 | 68.6 | 77.1 | 88.9 |
|  | Voclosporin 23.7 mg BID | 59 | 1 | 11 | 3 | 70 | 4 | 98.3 | 21.4 | 84.3 | 75.0 |
|  | Voclosporin 39.5 mg BID | 53 | 9 | 12 | 7 | 65 | 16 | 85.5 | 36.8 | 81.5 | 43.8 |
| 26 | Placebo | 34 | 5 | 12 | 18 | 46 | 23 | 87.2 | 60.0 | 73.9 | 78.3 |
|  | Voclosporin 23.7 mg BID | 54 | 1 | 7 | 5 | 61 | 6 | 98.2 | 41.7 | 88.5 | 83.3 |
|  | Voclosporin 39.5 mg BID | 58 | 3 | 11 | 5 | 69 | 8 | 95.1 | 31.3 | 84.1 | 62.5 |
| 36 | Placebo | 41 | 1 | 14 | 17 | 55 | 18 | 97.6 | 54.8 | 74.5 | 94.4 |
|  | Voclosporin 23.7 mg BID | 60 | 1 | 10 | 3 | 70 | 4 | 98.4 | 23.1 | 85.7 | 75.0 |
|  | Voclosporin 39.5 mg BID | 61 | 2 | 11 | 7 | 72 | 9 | 96.8 | 38.9 | 84.7 | 77.8 |
| 48 | Placebo | 37 | 1 | 5 | 21 | 42 | 22 | 97.4 | 80.8 | 88.1 | 95.5 |
|  | Voclosporin 23.7 mg BID | 58 | 0 | 8 | 3 | 66 | 3 | 100.0 | 27.3 | 87.9 | 100.0 |
|  | Voclosporin 39.5 mg BID | 61 | 0 | 5 | 11 | 66 | 11 | 100.0 | 68.8 | 92.4 | 100.0 |

TABLE 8

Table 8 - Early 35% reduction in UPCR

| Week | Treatment Group | Week 48 Partial Remission Early Drop | Week 48 Partial Remission No Early Drop | No Week 48 Partial Remission Early Drop | No Week 48 Partial Remission No Early Drop | Early Reduction Yes | Early Reduction No | Sensitivity | Specificity | Positive Predictive Value | Negative Predictive Value |
|---|---|---|---|---|---|---|---|---|---|---|---|
| 2 | Placebo | 13 | 29 | 13 | 31 | 26 | 60 | 31.0 | 70.5 | 50.0 | 51.7 |
|  | Voclosporin 23.7 mg BID | 36 | 25 | 6 | 18 | 42 | 43 | 59.0 | 75.0 | 85.7 | 41.9 |
|  | Voclosporin 39.5 mg BID | 28 | 32 | 11 | 13 | 39 | 45 | 46.7 | 54.2 | 71.8 | 28.9 |
| 4 | Placebo | 26 | 15 | 9 | 32 | 35 | 47 | 63.4 | 78.0 | 74.3 | 68.1 |
|  | Voclosporin 23.7 mg BID | 46 | 13 | 11 | 12 | 57 | 25 | 78.0 | 52.2 | 80.7 | 48.0 |
|  | Voclosporin 39.5 mg BID | 43 | 18 | 13 | 8 | 56 | 26 | 70.5 | 38.1 | 76.8 | 30.8 |
| 6 | Placebo | 30 | 12 | 14 | 25 | 44 | 37 | 71.4 | 64.1 | 68.2 | 67.6 |
|  | Voclosporin 23.7 mg BID | 47 | 12 | 9 | 9 | 56 | 21 | 79.7 | 50.0 | 83.9 | 42.9 |
|  | Voclosporin 39.5 mg BID | 47 | 16 | 14 | 6 | 61 | 22 | 74.6 | 30.0 | 77.0 | 27.3 |
| 8 | Placebo | 34 | 8 | 14 | 26 | 48 | 34 | 81.0 | 65.0 | 70.8 | 76.5 |
|  | Voclosporin 23.7 mg BID | 52 | 8 | 9 | 10 | 61 | 18 | 86.7 | 52.6 | 85.2 | 55.6 |
|  | Voclosporin 39.5 mg BID | 53 | 8 | 17 | 4 | 70 | 12 | 86.9 | 19.0 | 75.7 | 33.3 |

TABLE 8-continued

Table 8 - Early 35% reduction in UPCR

| Week | Treatment Group | Week 48 Partial Remission Early Drop | Week 48 Partial Remission No Early Drop | No Week 48 Partial Remission Early Drop | No Week 48 Partial Remission No Early Drop | Early Reduction Yes | Early Reduction No | Sensitivity | Specificity | Positive Predictive Value | Negative Predictive Value |
|---|---|---|---|---|---|---|---|---|---|---|---|
| 12 | Placebo | 35 | 7 | 14 | 26 | 49 | 33 | 83.3 | 65.0 | 71.4 | 78.8 |
|  | Voclosporin 23.7 mg BID | 54 | 7 | 10 | 9 | 64 | 16 | 88.5 | 47.4 | 84.4 | 56.3 |
|  | Voclosporin 39.5 mg BID | 52 | 10 | 14 | 4 | 66 | 14 | 83.9 | 22.2 | 78.8 | 28.6 |
| 16 | Placebo | 39 | 3 | 13 | 26 | 52 | 29 | 92.9 | 66.7 | 75.0 | 89.7 |
|  | Voclosporin 23.7 mg BID | 57 | 4 | 11 | 7 | 68 | 11 | 93.4 | 38.9 | 83.8 | 63.6 |
|  | Voclosporin 39.5 mg BID | 55 | 8 | 13 | 7 | 68 | 15 | 87.3 | 35.0 | 80.9 | 46.7 |
| 20 | Placebo | 38 | 4 | 15 | 22 | 53 | 26 | 90.5 | 59.5 | 71.7 | 84.6 |
|  | Voclosporin 23.7 mg BID | 57 | 3 | 8 | 8 | 65 | 11 | 95.0 | 50.0 | 87.7 | 72.7 |
|  | Voclosporin 39.5 mg BID | 56 | 6 | 15 | 5 | 71 | 11 | 90.3 | 25.0 | 78.9 | 45.5 |
| 24 | Placebo | 37 | 3 | 10 | 25 | 47 | 28 | 92.5 | 71.4 | 78.7 | 89.3 |
|  | Voclosporin 23.7 mg BID | 59 | 1 | 8 | 6 | 67 | 7 | 98.3 | 42.9 | 88.1 | 85.7 |
|  | Voclosporin 39.5 mg BID | 53 | 9 | 12 | 7 | 65 | 16 | 85.5 | 36.8 | 81.5 | 43.8 |
| 26 | Placebo | 34 | 5 | 11 | 19 | 45 | 24 | 87.2 | 63.3 | 75.6 | 79.2 |
|  | Voclosporin 23.7 mg BID | 52 | 3 | 7 | 5 | 59 | 8 | 94.5 | 41.7 | 88.1 | 62.5 |
|  | Voclosporin 39.5 mg BID | 55 | 6 | 11 | 5 | 66 | 11 | 90.2 | 31.3 | 83.3 | 45.5 |
| 36 | Placebo | 41 | 1 | 12 | 19 | 53 | 20 | 97.6 | 61.3 | 77.4 | 95.0 |
|  | Voclosporin 23.7 mg BID | 60 | 1 | 9 | 4 | 69 | 5 | 98.4 | 30.8 | 87.0 | 80.0 |
|  | Voclosporin 39.5 mg BID | 61 | 2 | 11 | 7 | 72 | 9 | 96.8 | 38.9 | 84.7 | 77.8 |
| 48 | Placebo | 37 | 1 | 3 | 23 | 40 | 24 | 97.4 | 88.5 | 92.5 | 95.8 |
|  | Voclosporin 23.7 mg BID | 58 | 0 | 7 | 4 | 65 | 4 | 100.0 | 36.4 | 89.2 | 100.0 |
|  | Voclosporin 39.5 mg BID | 61 | 0 | 4 | 12 | 65 | 12 | 100.0 | 75.0 | 93.8 | 100.0 |

Thus it appears the 8 week or 12 week results, for example, are predictions of ultimate outcome, and it is beneficial to stop treatment if there was no reduction in UPCR by >15% at that time.

For completeness, Tables 9a and 9b show similar results for an 8 week early time point when a 25% UPCR reduction is used as a criterion and the protocol extends for 24 or 48 weeks.

TABLE 9a

Probability of attaining a CR by Proteinuria if UPCR reduction of 25% or greater is achieved at 8 weeks:

| Group | # of patients in treatment arm (number with week 8 assessment) | # of CRs by Proteinuria at 24 weeks | # of patients with UPCR reduction of ≥25% at 8 weeks | #(%) of patients who had a reduction of UPCR of ≥25% who went on to be a CR by UPCR at 24 weeks | #(%) of patients who had a reduction of UPCR of ≥25% who went on to be a CR by UPCR at 48 weeks |
|---|---|---|---|---|---|
| Placebo | 88 (83) | 17 | 52 | 16/52 (30.8) | 18/52 (34.6) |
| Low Dose | 89 (80) | 29 | 64 | 29/64 (45.3) | 40/64 (62.5) |
| High Dose | 88 (84) | 24 | 72 | 24/72 (33.3) | 32/72 (44.4) |

TABLE 9b

Probability of attaining a CR by Proteinuria if UPCR reduction of 25% or greater is not achieved at 8 weeks:

| Group | # of patients in treatment arm (number with week 8 assessment) | # of CRs by Proteinuria at 24 weeks | # of patients without UPCR reduction of ≥25% at 8 weeks | #(%) of patients who did not have a reduction of UPCR of ≥25% who went on to be a CR by UPCR at 24 weeks | #(%) of patients who did not have a reduction of UPCR of ≥25% who went on to be a CR by UPCR at 48 weeks |
|---|---|---|---|---|---|
| Placebo | 88 (83) | 17 | 31 | 1/31 (3.2) | 3/31 (9.7) |
| Low Dose | 89 (80) | 29 | 16 | 0/16 (0.0) | 4/16 (25.0) |
| High Dose | 88 (84) | 24 | 12 | 0/12 (0.0) | 3/12 (25.0) |

Another criterion for effectiveness is normalization of C3 and/or C4 concentration in blood. The normal concentration of C3 is 90 mg/dl or greater and for C4 16 mg/dl or greater. Subjects for the treatment of the invention generally have concentrations below these values. Normalization of C3 is defined as an increase from below 90 mg/dl to above that level or a 25% increase from the baseline (below 90) exhibited by the subject and normalization of C4 is defined as an increase from below 16 mg/dl to above that level or a 25% increase from the baseline (below 16) exhibited by the subject.

Tables 10-12 provide similar data for these criteria to the data in Tables 4-9 for UPCR.

TABLE 10

Table 10 - Early C3 normalization

| Week | Treatment Group | Week 48 Partial Remission Normalization | Week 48 Partial Remission No Normalization | No Week 48 Partial Remission Normalization | No Week 48 Partial Remission No Normalization | Normalization Yes | Normalization No | Sensitivity | Specificity | Positive Predictive Value | Negative Predictive Value |
|---|---|---|---|---|---|---|---|---|---|---|---|
| 12 | Placebo | 16 | 24 | 15 | 22 | 31 | 46 | 40.0 | 59.5 | 51.6 | 47.8 |
|  | Voclosporin 23.7 mg BID | 23 | 34 | 8 | 10 | 31 | 44 | 40.4 | 55.6 | 74.2 | 22.7 |
|  | Voclosporin 39.5 mg BID | 34 | 28 | 7 | 10 | 41 | 38 | 54.8 | 58.8 | 82.9 | 26.3 |
| 24 | Placebo | 17 | 22 | 16 | 18 | 33 | 40 | 43.6 | 52.9 | 51.5 | 45.0 |
|  | Voclosporin 23.7 mg BID | 24 | 33 | 6 | 8 | 30 | 41 | 42.1 | 57.1 | 80.0 | 19.5 |
|  | Voclosporin 39.5 mg BID | 35 | 26 | 6 | 12 | 41 | 38 | 57.4 | 66.7 | 85.4 | 31.6 |
| 48 | Placebo | 15 | 23 | 14 | 13 | 29 | 36 | 39.5 | 48.1 | 51.7 | 36.1 |
|  | Voclosporin 23.7 mg BID | 25 | 30 | 2 | 8 | 27 | 38 | 45.5 | 80.0 | 92.6 | 21.1 |
|  | Voclosporin 39.5 mg BID | 34 | 29 | 7 | 9 | 41 | 38 | 54.0 | 56.3 | 82.9 | 23.7 |

TABLE 11

Table 11 - Early C4 normalization

| Week | Treatment Group | Week 48 Partial Remission Normalization | Week 48 Partial Remission No Normalization | No Week 48 Partial Remission Normalization | No Week 48 Partial Remission No Normalization | Normalization Yes | Normalization No | Sensitivity | Specificity | Positive Predictive Value | Negative Predictive Value |
|---|---|---|---|---|---|---|---|---|---|---|---|
| 12 | Placebo | 15 | 25 | 19 | 18 | 34 | 43 | 37.5 | 48.6 | 44.1 | 41.9 |
|  | Voclosporin 23.7 mg BID | 27 | 29 | 10 | 8 | 37 | 37 | 48.2 | 44.4 | 73.0 | 21.6 |
|  | Voclosporin 39.5 mg BID | 40 | 22 | 8 | 9 | 48 | 31 | 64.5 | 52.9 | 83.3 | 29.0 |

TABLE 11-continued

Table 11 - Early C4 normalization

| Week | Treatment Group | Week 48 Partial Remission Normalization | | No Week 48 Partial Remission Normalization | | Normalization | | Sensitivity | Specificity | Positive Predictive Value | Negative Predictive Value |
|---|---|---|---|---|---|---|---|---|---|---|---|
| | | Normal-ization | No Normal-ization | Normal-ization | No Normal-ization | Yes | No | | | | |
| 24 | Placebo | 16 | 23 | 18 | 16 | 34 | 39 | 41.0 | 47.1 | 47.1 | 41.0 |
| | Voclosporin 23.7 mg BID | 32 | 25 | 8 | 6 | 40 | 31 | 56.1 | 42.9 | 80.0 | 19.4 |
| | Voclosporin 39.5 mg BID | 39 | 22 | 5 | 13 | 44 | 35 | 63.9 | 72.2 | 88.6 | 37.1 |
| 48 | Placebo | 16 | 22 | 14 | 13 | 30 | 35 | 42.1 | 48.1 | 53.3 | 37.1 |
| | Voclosporin 23.7 mg BID | 29 | 26 | 5 | 5 | 34 | 31 | 52.7 | 50.0 | 85.3 | 16.1 |
| | Voclosporin 39.5 mg BID | 36 | 27 | 5 | 11 | 41 | 38 | 57.1 | 68.8 | 87.8 | 28.9 |

TABLE 12

Table 12 - Early C3/C4 normalization

| Week | Treatment Group | Week 48 Partial Remission | | No Week 48 Partial Remission | | Normalization | | Sensitivity | Specificity | Positive Predictive Value | Negative Predictive Value |
|---|---|---|---|---|---|---|---|---|---|---|---|
| | | Normal-ization | No Normal-ization | Normal-ization | No Normal-ization | Yes | No | | | | |
| 12 | Placebo | 11 | 29 | 14 | 23 | 25 | 52 | 27.5 | 62.2 | 44.0 | 44.2 |
| | Voclosporin 23.7 mg BID | 20 | 37 | 6 | 12 | 26 | 49 | 35.1 | 66.7 | 76.9 | 24.5 |
| | Voclosporin 39.5 mg BID | 29 | 33 | 7 | 10 | 36 | 43 | 46.8 | 58.8 | 80.6 | 23.3 |
| 24 | Placebo | 12 | 27 | 14 | 20 | 26 | 47 | 30.8 | 58.8 | 46.2 | 42.6 |
| | Voclosporin 23.7 mg BID | 23 | 34 | 4 | 10 | 27 | 44 | 40.4 | 71.4 | 85.2 | 22.7 |
| | Voclosporin 39.5 mg BID | 26 | 35 | 5 | 13 | 31 | 48 | 42.6 | 72.2 | 83.9 | 27.1 |
| 48 | Placebo | 10 | 28 | 10 | 17 | 20 | 45 | 26.3 | 63.0 | 50.0 | 37.8 |
| | Voclosporin 23.7 mg BID | 20 | 35 | 2 | 8 | 22 | 43 | 36.4 | 80.0 | 90.9 | 18.6 |
| | Voclosporin 39.5 mg BID | 27 | 36 | 5 | 11 | 32 | 47 | 42.9 | 68.8 | 84.4 | 23.4 |

Tables 13-17 make similar calculations for the combined results of UPCR and C3/C4 at 12 weeks. In these tables, the data from the 12 week determinations in Tables 4-8 are meshed with the data from the 12 week time point in Table 12.

Based on the levels of sensitivity, specificity, positive predictive value and negative predicted value shown, decision to stop or continue treatment is made.

TABLE 13

Table 13 - Early 15% reduction in UPCR or C3/C4 normalization

| Week | Treatment Group | Week 48 Partial Remission | | No Week 48 Partial Remission | | Early Drop or Normal | | Sensitivity | Specificity | Positive Predictive Value | Negative Predictive Value |
|---|---|---|---|---|---|---|---|---|---|---|---|
| | | Early Drop or Normal | No Early Drop or Normal | Early Drop or Normal | No Early Drop or Normal | Yes | No | | | | |
| 12 | Placebo | 39 | 3 | 26 | 12 | 65 | 15 | 92.9 | 31.6 | 60.0 | 80.0 |
| | Voclosporin 23.7 mg BID | 60 | 1 | 18 | 1 | 78 | 2 | 98.4 | 5.3 | 76.9 | 50.0 |

TABLE 13-continued

Table 13 - Early 15% reduction in UPCR or C3/C4 normalization

| Week | Treatment Group | Week 48 Partial Remission | | No Week 48 Partial Remission | | Early Drop or Normal | | Sensitivity | Specificity | Positive Predictive Value | Negative Predictive Value |
|---|---|---|---|---|---|---|---|---|---|---|---|
| | | Early Drop or Normal | No Early Drop or Normal | Early Drop or Normal | No Early Drop or Normal | Yes | No | | | | |
| | Voclosporin 39.5 mg BID | 60 | 3 | 16 | 3 | 76 | 6 | 95.2 | 15.8 | 78.9 | 50.0 |
| 24 | Placebo | 39 | 2 | 27 | 8 | 66 | 10 | 95.1 | 22.9 | 59.1 | 80.0 |
| | Voclosporin 23.7 mg BID | 61 | 0 | 13 | 1 | 74 | 1 | 100.0 | 7.1 | 82.4 | 100.0 |
| | Voclosporin 39.5 mg BID | 57 | 5 | 15 | 4 | 72 | 9 | 91.9 | 21.1 | 79.2 | 44.4 |
| 48 | Placebo | 37 | 1 | 18 | 9 | 55 | 10 | 97.4 | 33.3 | 67.3 | 90.0 |
| | Voclosporin 23.7 mg BID | 58 | 0 | 10 | 1 | 68 | 1 | 100.0 | 9.1 | 85.3 | 100.0 |
| | Voclosporin 39.5 mg BID | 62 | 0 | 12 | 4 | 74 | 4 | 100.0 | 25.0 | 83.8 | 100.0 |

TABLE 14

Table 14 - Early 20% reduction in UPCR or C3/C4 normalization

| Week | Treatment Group | Week 48 Partial Remission | | No Week 48 Partial Remission | | Early Drop or Normal | | Sensitivity | Specificity | Positive Predictive Value | Negative Predictive Value |
|---|---|---|---|---|---|---|---|---|---|---|---|
| | | Early Drop or Normal | No Early Drop or Normal | Early Drop or Normal | No Early Drop or Normal | Yes | No | | | | |
| 12 | Placebo | 38 | 4 | 26 | 12 | 64 | 16 | 90.5 | 31.6 | 59.4 | 75.0 |
| | Voclosporin 23.7 mg BID | 60 | 1 | 17 | 2 | 77 | 3 | 98.4 | 10.5 | 77.9 | 66.7 |
| | Voclosporin 39.5 mg BID | 60 | 3 | 16 | 3 | 76 | 6 | 95.2 | 15.8 | 78.9 | 50.0 |
| 24 | Placebo | 39 | 2 | 25 | 10 | 64 | 12 | 95.1 | 28.6 | 60.9 | 83.3 |
| | Voclosporin 23.7 mg BID | 61 | 0 | 13 | 1 | 74 | 1 | 100.0 | 7.1 | 82.4 | 100.0 |
| | Voclosporin 39.5 mg BID | 57 | 5 | 15 | 4 | 72 | 9 | 91.9 | 21.1 | 79.2 | 44.4 |
| 48 | Placebo | 37 | 1 | 17 | 10 | 54 | 11 | 97.4 | 37.0 | 68.5 | 90.9 |
| | Voclosporin 23.7 mg BID | 58 | 0 | 10 | 1 | 68 | 1 | 100.0 | 9.1 | 85.3 | 100.0 |
| | Voclosporin 39.5 mg BID | 62 | 0 | 12 | 4 | 74 | 4 | 100.0 | 25.0 | 83.8 | 100.0 |

TABLE 15

Table 15 - Early 25% reduction in UPCR or C3/C4 normalization

| Week | Treatment Group | Week 48 Partial Remission | | No Week 48 Partial Remission | | Early Drop or Normal | | Sensitivity | Specificity | Positive Predictive Value | Negative Predictive Value |
|---|---|---|---|---|---|---|---|---|---|---|---|
| | | Early Drop or Normal | No Early Drop or Normal | Early Drop or Normal | No Early Drop or Normal | Yes | No | | | | |
| 12 | Placebo | 38 | 4 | 24 | 14 | 62 | 18 | 90.5 | 36.8 | 61.3 | 77.8 |
| | Voclosporin 23.7 mg BID | 58 | 2 | 16 | 3 | 74 | 5 | 96.7 | 15.8 | 78.4 | 60.0 |
| | Voclosporin 39.5 mg BID | 60 | 3 | 16 | 3 | 76 | 6 | 95.2 | 15.8 | 78.9 | 50.0 |
| 24 | Placebo | 39 | 2 | 23 | 12 | 62 | 14 | 95.1 | 34.3 | 62.9 | 85.7 |
| | Voclosporin 23.7 mg BID | 61 | 0 | 13 | 1 | 74 | 1 | 100.0 | 7.1 | 82.4 | 100.0 |

TABLE 15-continued

Table 15 - Early 25% reduction in UPCR or C3/C4 normalization

| Week | Treatment Group | Week 48 Partial Remission | | No Week 48 Partial Remission | | Early Drop or Normal | | Sensitivity | Specificity | Positive Predictive Value | Negative Predictive Value |
|---|---|---|---|---|---|---|---|---|---|---|---|
| | | Early Drop or Normal | No Early Drop or Normal | Early Drop or Normal | No Early Drop or Normal | Yes | No | | | | |
| | Voclosporin 39.5 mg BID | 57 | 5 | 14 | 5 | 71 | 10 | 91.9 | 26.3 | 80.3 | 50.0 |
| 48 | Placebo | 37 | 1 | 17 | 10 | 54 | 11 | 97.4 | 37.0 | 68.5 | 90.9 |
| | Voclosporin 23.7 mg BID | 58 | 0 | 10 | 1 | 68 | 1 | 100.0 | 9.1 | 85.3 | 100.0 |
| | Voclosporin 39.5 mg BID | 62 | 0 | 10 | 6 | 72 | 6 | 100.0 | 37.5 | 86.1 | 100.0 |

TABLE 16

Table 16 - Early 30% reduction in UPCR or C3/C4 normalization

| Week | Treatment Group | Week 48 Partial Remission | | No Week 48 Partial Remission | | Early Drop or Normal | | Sensitivity | Specificity | Positive Predictive Value | Negative Predictive Value |
|---|---|---|---|---|---|---|---|---|---|---|---|
| | | Early Drop or Normal | No Early Drop or Normal | Early Drop or Normal | No Early Drop or Normal | Yes | No | | | | |
| 12 | Placebo | 37 | 5 | 24 | 14 | 61 | 19 | 88.1 | 36.8 | 60.7 | 73.7 |
| | Voclosporin 23.7 mg BID | 58 | 2 | 16 | 3 | 74 | 5 | 96.7 | 15.8 | 78.4 | 60.0 |
| | Voclosporin 39.5 mg BID | 59 | 4 | 16 | 3 | 75 | 7 | 93.7 | 15.8 | 78.7 | 42.9 |
| 24 | Placebo | 39 | 2 | 22 | 13 | 61 | 15 | 95.1 | 37.1 | 63.9 | 86.7 |
| | Voclosporin 23.7 mg BID | 61 | 0 | 13 | 1 | 74 | 1 | 100.0 | 7.1 | 82.4 | 100.0 |
| | Voclosporin 39.5 mg BID | 57 | 5 | 14 | 5 | 71 | 10 | 91.9 | 26.3 | 80.3 | 50.0 |
| 48 | Placebo | 37 | 1 | 13 | 14 | 50 | 15 | 97.4 | 51.9 | 74.0 | 93.3 |
| | Voclosporin 23.7 mg BID | 58 | 0 | 9 | 2 | 67 | 2 | 100.0 | 18.2 | 86.6 | 100.0 |
| | Voclosporin 39.5 mg BID | 62 | 0 | 8 | 8 | 70 | 8 | 100.0 | 50.0 | 88.6 | 100.0 |

TABLE 17

Table 17 - Early 35% reduction in UPCR or C3/C4 normalization

| Week | Treatment Group | Week 48 Partial Remission | | No Week 48 Partial Remission | | Early Drop or Normal | | Sensitivity | Specificity | Positive Predictive Value | Negative Predictive Value |
|---|---|---|---|---|---|---|---|---|---|---|---|
| | | Early Drop or Normal | No Early Drop or Normal | Early Drop or Normal | No Early Drop or Normal | Yes | No | | | | |
| 12 | Placebo | 36 | 6 | 23 | 15 | 59 | 21 | 85.7 | 39.5 | 61.0 | 71.4 |
| | Voclosporin 23.7 mg BID | 56 | 4 | 14 | 5 | 70 | 9 | 93.3 | 26.3 | 80.0 | 55.6 |
| | Voclosporin 39.5 mg BID | 57 | 6 | 16 | 3 | 73 | 9 | 90.5 | 15.8 | 78.1 | 33.3 |
| 24 | Placebo | 39 | 2 | 21 | 14 | 60 | 16 | 95.1 | 40.0 | 65.0 | 87.5 |
| | Voclosporin 23.7 mg BID | 61 | 0 | 10 | 4 | 71 | 4 | 100.0 | 28.6 | 85.9 | 100.0 |
| | Voclosporin 39.5 mg BID | 57 | 5 | 14 | 5 | 71 | 10 | 91.9 | 26.3 | 80.3 | 50.0 |

TABLE 17-continued

Table 17 - Early 35% reduction in UPCR or C3/C4 normalization

| Week | Treatment Group | Week 48 Partial Remission | | No Week 48 Partial Remission | | Early Drop or Normal | | Sensitivity | Specificity | Positive Predictive Value | Negative Predictive Value |
|---|---|---|---|---|---|---|---|---|---|---|---|
| | | Early Drop or Normal | No Early Drop or Normal | Early Drop or Normal | No Early Drop or Normal | Yes | No | | | | |
| 48 | Placebo | 37 | 1 | 12 | 15 | 49 | 16 | 97.4 | 55.6 | 75.5 | 93.8 |
| | Voclosporin 23.7 mg BID | 58 | 0 | 8 | 3 | 66 | 3 | 100.0 | 27.3 | 87.9 | 100.0 |
| | Voclosporin 39.5 mg BID | 62 | 0 | 7 | 9 | 69 | 9 | 100.0 | 56.3 | 89.9 | 100.0 |

EXAMPLE 4

Low Dose Corticosteroid

Applicants have also found that the dosage of corticosteroid can effectively be reduced as compared to "standard of care" as shown in Tables 8 and 9, and can be reduced further to 4 mg per day or less.

TABLE 18

Standard of Care Dosing Schedule for IV methylprednisolone and daily oral prednisone:

| Time | Patients <45 kg (daily dosage) | Patients ≥45 kg (daily dosage) |
|---|---|---|
| Days 1-3 | 0.5 g IV methylprednisolone | 1 g IV methylprednisolone |
| Days 3-112 | 1 mg/kg tapered down | 1 mg/kg (maximum 80 mg) tapered down |

TABLE 19

Lowered Dosing Schedule for IV methylprednisolone and daily oral prednisone:

| Time | Patients <45 kg (daily dosage) | Patients ≥45 kg (daily dosage) |
|---|---|---|
| Days 1-2 | 0.25 g IV methylprednisolone | 0.5 g IV methylprednisolone |
| Days 3-13 | 20 mg oral prednisone | 25 mg oral prednisone |
| Week 3 | 15 mg oral prednisone | 20 mg oral prednisone |
| Week 4 | 10 mg oral prednisone | 15 mg oral prednisone |
| Week 6 | 10 mg oral prednisone | 10 mg oral prednisone |
| Week 8 | 5 mg oral prednisone | 5 mg oral prednisone |
| Week 12 | 5 mg oral prednisone | 5 mg oral prednisone |
| Week 16 | 2.5 mg oral prednisone | 2.5 mg oral prednisone |

The invention claimed is:

1. A method of treating lupus nephritis (LN) in a subject, the method comprising:
   a) selecting for treatment a subject having LN, the selecting comprising determining the subject's estimated Glomerular Filtration Rate (eGFR) at a first time point prior to initiating administering step b);
   b) administering to the subject voclosporin, mycophenolate mofetil (MMF), and corticosteroids, wherein the administering comprises administering the voclosporin at a starting dose of 23.7 mg administered orally twice daily (BID);
   c) assessing the subject's eGFR at a second time point after initiating the administering step b); and
   d) administering to the subject a reduced dose of 15.8 mg BID or 7.9 mg BID voclosporin to treat LN in the subject if, between the first and the second time points, the subject's eGFR decreases in the range of >20% to <30% below the subject's eGFR at the first time point to below 60 ml/min/1.73 m².

2. The method of claim 1, comprising continuing the administering step b) for a period of at least 16 weeks and wherein the corticosteroids dose is not more than 2.5 mg/day by week 16.

3. The method of claim 1, wherein the reduced dose is 15.8 mg BID.

4. The method of claim 1, wherein the voclosporin is a mixture of at least 90% E isomer and not more than 10% Z isomer.

5. The method of claim 1, wherein the corticosteroids are methylprednisolone and/or prednisone.

6. The method of claim 1, comprising continuing the administering step b) for a period of at least 16 weeks.

7. The method of claim 1, comprising continuing the administering step b) for a period of at least 24 weeks.

8. The method of claim 1, comprising continuing the administering step b) for a period of at least 48 weeks.

9. The method of claim 1, comprising continuing the administering step b) for a period of at least 52 weeks.

10. The method of claim 1, wherein the selecting step a) further comprises determining the subject's UPCR prior to initiating the administering step b), and selecting a subject having LN that has a urine protein to creatinine ratio (UPCR) of ≥1.5 mg/mg.

11. The method of claim 1, wherein the selecting step a) comprises selecting a subject that has an eGFR of ≥45 mL/min/1.73 m² at the first time point.

12. The method of claim 1, further comprising assessing the subject's eGFR at a third time point after initiating step d), and administering to the subject a reduced dose of 15.8 mg BID or 7.9 mg BID voclosporin if, between the first and the third time points, the eGFR of the subject decreases in the range of >20% to <30% below the subject's eGFR at the first time point to below 60 ml/min/1.73 m².

13. The method of claim 1, comprising continuing to administer to the subject the dose of 23.7 mg BID voclosporin to treat LN in the subject if, between the first and the second time points, the subject's eGFR decreases by ≤20% below the subject's eGFR at the first time point.

14. A method of treating lupus nephritis (LN) in a subject, the method comprising:
- a) selecting for treatment a subject having LN, the selecting comprising determining the subject's estimated Glomerular Filtration Rate (eGFR) at a first time point prior to initiating administering step b);
- b) administering to the subject voclosporin, mycophenolate mofetil (MMF), and corticosteroids, wherein the administering comprises administering the voclosporin at a starting dose of 23.7 mg administered orally twice daily (BID);
- c) assessing the subjects eGFR at a second time point after initiating the administering step b); and
- d) administering to the subject a reduced dose of 15.8 mg BID or 7.9 mg BID voclosporin to treat LN in the subject if, between the first and the second time points, the subjects eGFR decreases in the range of >20% to <30% below the subject's eGFR at the first time point to below 60 ml/min/1.73 m$^2$, and wherein the administering of d) achieves a urine protein creatinine ratio (UPCR) of <0.5 mg/mg.

15. The method of claim 1, wherein the reduced dose is 7.9 mg BID.

16. The method of claim 14, comprising continuing to administer to the subject the dose of 23.7 mg BID voclosporin to treat LN in the subject if, between the first and the second time points, the subject's eGFR decreases by ≤20% below the subject's eGFR at the first time point.

17. The method of claim 14, comprising continuing the administering step b) for a period of at least 16 weeks and wherein the corticosteroids dose is not more than 2.5 mg/day by week 16.

18. The method of claim 14, wherein the reduced dose is 15.8 mg BID.

19. The method of claim 14, wherein the voclosporin is a mixture of at least 90% E isomer and not more than 10% Z isomer.

20. The method of claim 14, wherein the corticosteroids are methylprednisolone and/or prednisone.

21. The method of claim 14, comprising continuing the administering step b) for a period of at least 16 weeks.

22. The method of claim 14, comprising continuing the administering step b) for a period of at least 24 weeks.

23. The method of claim 14, comprising continuing the administering step b) for a period of at least 48 weeks.

24. The method of claim 14, comprising continuing the administering step b) for a period of at least 52 weeks.

25. The method of claim 14, wherein the selecting step a) further comprises determining the subject's UPCR prior to initiating the administering step b), and selecting a subject having LN that has a urine protein to creatinine ratio (UPCR) of ≥1.5 mg/mg.

26. The method of claim 14, wherein the selecting step a) comprises selecting a subject that has an eGFR of ≥45 mL/min/1.73 m$^2$ at the first time point.

27. The method of claim 14, wherein the reduced dose is 7.9 mg BID.

* * * * *

UNITED STATES PATENT AND TRADEMARK OFFICE
CERTIFICATE OF CORRECTION

PATENT NO. : 11,622,991 B2  
APPLICATION NO. : 17/713140  
DATED : April 11, 2023  
INVENTOR(S) : Neil Solomons et al.

Page 1 of 1

It is certified that error appears in the above-identified patent and that said Letters Patent is hereby corrected as shown below:

On the Title Page

At the left column, under (71) Applicant, "Aurinia Pharmaceuticals Inc., Victoria (CA)" should read -- Aurinia Pharmaceuticals Inc., Edmonton (CA) --;

At the right column, Line 4 under OTHER PUBLICATIONS, "Eurpean Medicine Agency" should read -- European Medicine Agency --;

At the right column, Line 7 under OTHER PUBLICATIONS, "Immunosupressors" should read -- Immunosuppressors --;

In the Claims

At Claim 14, Column 35, Line 12, "the subjects" should read -- the subject's --; and At Claim 14, Column 35, Line 17, "the subjects" should read -- the subject's --.

Signed and Sealed this  
Twentieth Day of June, 2023

Katherine Kelly Vidal  
*Director of the United States Patent and Trademark Office*